United States Patent [19]

Hubschwerlen et al.

[11] Patent Number: 5,698,577
[45] Date of Patent: Dec. 16, 1997

[54] COMPOSITIONS OF BICYCLIC β-LACTAMS AND USES THEREOF

[75] Inventors: Christian Hubschwerlen, Durmenach; Robert Charnas, Hesingue, both of France; Ingrid Heinze, Merzhausen; Klaus Gubernator, Freiburg, both of Germany

[73] Assignee: Hoffmann-La Roche Inc., Nutley, N.J.

[21] Appl. No.: 421,574

[22] Filed: Apr. 12, 1995

Related U.S. Application Data

[62] Division of Ser. No. 163,611, Dec. 6, 1993, abandoned, which is a continuation of Ser. No. 959,197, Oct. 9, 1992, abandoned, which is a continuation-in-part of Ser. No. 862,678, Apr. 3, 1992, abandoned.

[30] Foreign Application Priority Data

Apr. 11, 1991 [CH] Switzerland .................... 1083/91
Feb. 13, 1992 [CH] Switzerland ..................... 429/92

[51] Int. Cl.$^6$ .................... A61K 31/40; A61K 31/43; A61K 31/545; A61K 31/395
[52] U.S. Cl. .................... 514/408; 514/192; 514/198; 514/199; 514/200; 514/206; 514/210
[58] Field of Search .................... 514/192, 198, 514/199, 200, 206, 210, 408

[56] References Cited

U.S. PATENT DOCUMENTS

5,510,343  4/1996  Charnas et al. .................... 514/210

FOREIGN PATENT DOCUMENTS

076 758  10/1982  European Pat. Off. .
088 488   1/1983  European Pat. Off. .
232 017   1/1987  European Pat. Off. .
2202-891  2/1989  Japan .

OTHER PUBLICATIONS

Derwent Abstract No. 90–287151/38 of Japanese KOKAI 2202-891.

Hackh's Chemical Dictionary, Fourth Edition, p. 36 (1969).

Kametani, Tetsuji, et al., Chemical Abstracts, vol. 100, No. 19, Abstract No. 156408h (May 7, 1994).

The Van Nostrand Chemist's Dictionary, p. 28 and p. 311 (1953).

Stryer, L., *Biochemistry*, 2nd. Ed., Freeman and Co., p. 13 (1975).

*Primary Examiner*—Kevin E. Weddington
*Attorney, Agent, or Firm*—George W. Johnston; Dennis P. Tramaloni; Alan P. Kass

[57] ABSTRACT

There are described pharmaceutical compositions comprising
(a) compounds of the formula

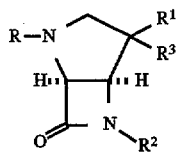

I in which R signifies lower alkoxycarbonyl, lower alkoxy-carbonylamino, the acyl residue of an α- or β-amino acid or a residue of the general formula

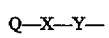 (a)

wherein Q signifies a 3- to 6-membered ring which optionally contains nitrogen, sulphur and/or oxygen and which is optionally bonded with a fused ring, X signifies a direct bond or a linear "spacer" with up to 6 atoms consisting of carbon, nitrogen, oxygen and/or sulphur, of which up to 2 atoms can be nitrogen atoms and 1 atom can be oxygen or sulphur, and Y represents one of the groups —CO—, —CS—, —CONH— and (where X contains neither sulphur nor carbonyl as a terminal component) —SO$_2$—; and in which R$^1$ signifies hydrogen, halogen, carbamoyloxy, lower alkanoyloxy or a group of the formula —S—Het, wherein Het represents a 5- or 6-membered heteroaromatic group containing nitrogen, sulphur and/or oxygen, and R$^2$ represents the sulpho group —SO$_3$H and in which R$^3$ represents hydrogen or R$^1$ and R$^3$ together represent a group of the formula

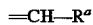 (c)

wherein R$^a$ signifies one of the groups

—COR$^b$   (c$^1$)
—CH$_2$—OCOR$^c$   (c$^2$)
—CH$_2$—NR$^d$R$^e$   (c$^3$)
—CH$_2$—S—Het   (c$^4$)

in which R$^b$ represents lower alkoxy or amino, R$^c$ represents lower alkyl, phenyl or amino, R$^d$ and R$^e$ each independently represent hydrogen or lower alkyl or R$^d$ and R$^e$ together with the N atom to which they are attached represent a 5- or 6-membered N-heterocycle which optionally contains a further nitrogen, oxygen or sulphur atom and Het represents a 5- or 6-membered heteroaromatic group containing nitrogen, sulphur and/ or oxygen; and
(b) a therapeutically effective amount of a β-lactam antibiotics or their pharmaceutically compatible salts; and a pharmaceutically compatible carrier and pharmaceutically compatible salts of these compounds.

The combination is useful in the control or prevention of illnesses caused by β-lactamase forming pathogens.

14 Claims, No Drawings

COMPOSITIONS OF BICYCLIC β-LACTAMS AND USES THEREOF

CROSS-REFERENCE TO RELATED APPLICATION

This is a division, of application Ser. No. 08/163,611, filed Dec. 6, 1993, now abandoned, which is a continuation of application Ser. No. 07/959,197, filed Oct. 9, 1992, now abandoned, which is a continuation-in-part of application Ser. No. 07/862,078, filed Apr. 3, 1992, now abandoned.

BACKGROUND OF THE INVENTION

FIELD OF THE INVENTION

The invention relates to bicyclic and tricyclic β-lactams and their pharmaceutically compatible salts.

SUMMARY OF THE INVENTION

The present invention is concerned with compounds having the formula

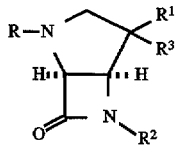

I in which R signifies lower alkoxycarbonyl, lower alkoxycarbonylamino, the acyl residue of an α- or β-amino acid or a residue of the formula

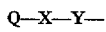  (a)

wherein Q signifies a 3- to 6-membered ring which optionally contains nitrogen, sulphur and/or oxygen and which is optionally bonded with a fused ring, X signifies a direct bond or a linear "spacer" with up to 6 atoms consisting of carbon, nitrogen, oxygen and/or sulphur, of which up to 2 atoms can be nitrogen atoms and 1 atom can be oxygen or sulphur, and Y represents one of the groups —CO—, —CS—, —CONH— and (where X contains neither sulphur nor carbonyl as a terminal component) —SO$_2$—; and in which R$^1$ signifies hydrogen, halogen, carbamoyloxy, lower alkanoyloxy or a group of the formula —S—Het, wherein Het represents a 5- or 6-membered heteroaromatic group containing nitrogen, sulphur and/or oxygen, and R$^2$ represents the sulpho group —SO$_3$H or R$^1$ and R$^2$ together signify a group of the formula

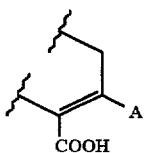  (b)

wherein A represents hydrogen or a residue which is usable in the 3-position of cephalosporin antibiotics, and in which R$^3$ represents hydrogen or R$^1$ and R$^3$ together represent a group of the formula =CH—R$^a$  (c)

wherein R$^a$ signifies one of the groups

—COR$^b$  (c$^1$)

—CH$_2$—OCOR$^c$  (c$^2$)

—CH$_2$—NR$^d$R$^e$  (c$^3$)

—CH$_2$—S—Het  (c$^4$)

in which R$^b$ represents lower alkoxy or amino, R$^c$ represents lower alkyl, phenyl or amino, R$^d$ and R$^e$ each independently represent hydrogen or lower alkyl or R$^d$ and R$^e$ together with the N atom to which they are attached represent a 5- or 6-membered N-heterocycle which optionally contains a further nitrogen, oxygen or sulphur atom and Het represents a 5- or 6-membered heteroaromatic group containing nitrogen, sulphur and/or oxygen, and pharmaceutically compatible salts of these compounds.

These compounds are novel and are distinguished by therapeutically valuable properties. In particular, they have pronounced β-lactamase inhibiting properties and are accordingly useful in combination with β-lactam antibiotics such as the penicillins and cephalosporins in the control of pathogens which form β-lactamase.

DETAILED DESCRIPTION OF THE INVENTION

The present invention is concerned with compounds having the formula

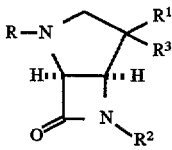

I in which R signifies lower alkoxycarbonyl, lower alkoxycarbonylamino, the acyl residue of an α- or β-amino acid or a residue of the formula

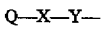  (a)

wherein Q signifies a 3- to 6-membered ring which optionally contains nitrogen, sulphur and/or oxygen and which is optionally bonded with a fused ring, X signifies a direct bond or a linear "spacer" with up to 6 atoms consisting of carbon, nitrogen, oxygen and/or sulphur, of which up to 2 atoms can be nitrogen atoms and 1 atom can be oxygen or sulphur, and Y represents one of the groups —CO—, —CS—, —CONH— and (where X contains neither sulphur nor carbonyl as a terminal component) —SO$_2$—; and in which R$^1$ signifies hydrogen, halogen, carbamoyloxy, lower alkanoyloxy or a group of the formula —S—Het, wherein Het represents a 5- or 6-membered heteroaromatic group containing nitrogen, sulphur and/or oxygen, and R$^2$ represents the sulpho group —SO$_3$H or R$^1$ and R$^2$ together signify a group of the formula

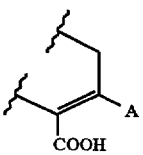  (b)

wherein A represents hydrogen or a residue which is usable in the 3-position of cephalosporin antibiotics, and in which R$^3$ represents hydrogen or R$^1$ and R$^3$ together represent a group of the formula =CH—R$^a$  (c)

wherein R$^a$ signifies one of the groups

—COR$^b$  (c$^1$)

—CH₂—OCOR^c  (c²)

—CH₂—NR^d R^e  (c³)

—CH₂—S—Het  (c⁴)

in which $R^b$ represents lower alkoxy or amino, $R^c$ represents lower alkyl, phenyl or amino, $R^d$ and $R^e$ each independently represent hydrogen or lower alkyl or $R^d$ and $R^e$ together with the N atom to which they are attached represent a 5- or 6-membered N-heterocycle which optionally contains a further nitrogen, oxygen or sulphur atom and Her represents a 5- or 6-membered heteroaromatic group containing nitrogen, sulphur and/or oxygen, and pharmaceutically compatible salts of these compounds.

These compounds are novel and are distinguished by therapeutically valuable properties. In particular, they have pronounced β-lactamase inhibiting properties and are accordingly useful in combination with β-lactam antibiotics such as the penicillins and cephalosporins in the control of pathogens which form β-lactamase. Those of ordinary skill in the art will appreciate that β-lactamase inhibitors possess the ability to inactivate β-lactamase by blocking the sites of these enzymes.

The term "lower alkyl" taken alone or in combinations such as "lower alkoxy", "lower alkylthio", "lower alkylsulphinyl", "lower alkylsulphonyl", "lower alkoxycarbonyl", "alkanoyloxy" and the like signifies straight-chain or branched saturated hydrocarbon residues with a maximum of 7, preferably a maximum of 4, carbon atoms such as methyl, ethyl, n-propyl, isopropyl, n-butyl, t-butyl and the like. "Halogen" signifies all four halogens, viz., bromine, chlorine, fluorine, and iodine, but preferably chlorine or fluorine. "Amino" can also be substituted, for example, by lower alkyl, such as methylamino and dimethylamino. "5- or 6-membered N-heterocycle optionally contains a further nitrogen, oxygen or sulphur atom" can also be N- or C-substituted, for example, by lower alkyl. Examples of saturated heterocycles include pyrrolidinyl, piperidinyl, piperazinyl, N-methylpiperazinyl, morpholinyl and thiomorpholinyl. Examples of aromatic heterocycles include residues which are derived from pyridine and (α, β or γ)-picoline, whereby a positive charge exists on the nitrogen atom ("zwitterion"). The term "Het" stands for a 5- or 6-membered heteroaromatic group such as for example, tetrazolyl, methyltetrazolyl, methylthiozolyl.

The R groups present in the compounds of formula I have the following significances a), b), c) and d):

a) Lower alkoxycarbonyl such as for example, methoxycarbonyl, ethoxycarbonyl or t-butoxycarbonyl.

b) Lower alkoxycarbonylamino such as for example, methoxycarbonylamino, ethoxycarbonylamino or t-butoxycarbonylamino.

c) The acyl residue of an α or β-amino acid, which can be not only a natural amino acid, such as, for example, alanine, arginine, asparagine, cysteine, glutamine, glutamic acid, glycine, histidine, isoleucine, leucine, lysine, methionine, phenylalanine, proline, serine, threonine, tryptophan, tyrosine, or valine, but also a non-natural amino acid, such as for example, an acyl group derived from glycine, alanine, β-alanine, methionine, leucine, isoleucine, ornithine, aspartic acid, arginine, lysine, serine, cystine, cysteine, valine, phenylalanine, 3-hydroxyproline, 4-hydroxyproline, proline, tyrosine, tryptophan, threonine, asparagine, glutamine, sarcosine, 2-(2-thienyl)-glycine, 2-(2-amino-4-thiazolyl)-glycine, histidine, 2-phenylglycine, p-hydroxyphenylglycine, m-hydroxyphenylglycine, o-fluorophenylglycine, m,p-dihydroxyphenylglycine or α-amino-cinnamic acid. The amino group can optionally be substituted, for example, by lower alkyl such as methyl or ethyl, by aryl, especially by phenyl (as in N-phenylglycyl), by acyl, especially by lower alkanoyl such as acetyl or propionyl, by benzoyl, benzyloxy-carbonyl, t-butoxycarbonyl or N-heterocyclylcarbonyl such as (4-ethyl-2,3-dioxo-1-piperazinyl)-carbonyl or (4-hydroxy-6-methyl-3-pyridyl)-carbonyl. Of the acyl residues of α- and β-amino acids those which are derived from an α-amino acid are preferred.

d) A residue of the formula

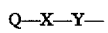  (a)

wherein Q, X and Y are defined above.

Q preferably signifies a 5- or 6-membered (hetero) aromatic ring which optionally contains nitrogen, sulphur and/or oxygen and which is optionally bonded with a further fused ring. Hetero-aromatic rings generally contain 1–4 nitrogen atoms and/or 1–2 sulphur or oxygen atoms. Examples of (hetero)aromatic rings for Q include: 2-furyl, 3-furyl, thiazolyl, thiadiazolyl, 2-thienyl, 3-thienyl, 2-pyrrolyl, 3-pyrrolyl, phenyl, 2-pyridyl, 3-pyridyl, 4-pyridyl, imidazolyl, pyrazolyl, triazolyl, tetrazolyl (for example, 1H-tetrazol-5-yl and 1H-tetrazol-1-yl), pyrazinyl, pyridazinyl and pyrimidinyl. The Q groups can also be substituted, for example, by lower alkyl, hydroxy, lower alkoxy, lower alkanoyloxy, sulphonyloxy, halogen, amino, dimethylamino or chloroacetylamino, for example, 4-tolyl, 3-methyl-(2-furyloxy), 1-methyl-1H-tetrazol-5-yl, 4-hydroxyphenyl, 4-anisyl, 3,4,5-trimethoxyphenyl, 4-chlorophenyl, 4-fluoro-(2-pyridyl), 2-amino-4-thiazolyl, 5-methyl-1,3,4-thiadiazol-2-yl, p-amino-phenyl, p-(chloroacetylamino)-phenyl, 3,4-disulphonyloxy-phenyl and 3,4-diacetoxyphenyl. A further ring can be fused on, especially a phenyl ring such as for example, in indolyl, 1H-benzotriazol-1-yl, 2-oxo-2H-1-benzopyran-7-yl or 2-oxo-4-(trifluoromethyl)-2H-1-benzopyran-7-yl, or also a 5- or 6-membered heterocycle such as for example, in benzimidazol-5-yl or 1H-benzotriazol-5-yl.

Those of ordinary skill in the art will appreciate that when Q signifies a 5- or 6-membered (hetero)aromatic ring which optionally contains nitrogen, sulphur, and/or oxygen, if Q does not contain nitrogen, sulphur and/or oxygen, then Q contains all carbon atoms and is a 5- or 6-membered aromatic ring. Examples include cyclopentadienyl anion and phenyl. If Q contains nitrogen, sulphur, and/or oxygen, then those of ordinary skill in the art will appreciate that Q would then signify a 5- or 6-membered heteroaromatic ring, examples of which are set forth above.

Q can, however, also signify a 3- to 6-membered (hetero)-saturated ring which optionally contains nitrogen, sulphur and/or oxygen. Heterocyclic rings generally contain 1–4 nitrogen atoms and/or 1–2 sulphur or oxygen atoms. Examples of (hetero)-saturated rings Q include: cyclopropyl, cyclobutyl, cyclopentyl, cyclohexyl, piperidyl, piperazinyl, morpholinyl, thiomorpholinyl, tetrahydrothienyl and tetrahydrofuryl. These groups can also be substituted, for example, by lower alkyl, oxo etc., for example, 4-methyl-1-pipera-zinyl and 2-oxo-3-tetrahydrothienyl.

Those of ordinary skill in the art will appreciate that when Q signifies a 3- to 6-membered (hetero)saturated ring which optionally contains nitrogen, sulphur and/or oxygen, if Q does not contain nitrogen, sulphur and/or oxygen, then Q contains all carbon atoms and is a 3- to 6-membered saturated ring, examples of which are set forth above. If Q contains nitrogen, sulphur, and/or oxygen, then those of ordinary skill in the art will appreciate that Q would then signify a 3- to 6-membered heterosaturated ring, examples of which are set forth above.

The "spacer" X present in the residue (a) of the formula Q—X—Y— can consist for example, of 1–6 carbon atoms, of 1 nitrogen atom and 0–5 carbon atoms, of 2 nitrogen atoms and 0–4 carbon atoms, of 1 oxygen atom and 0–5 carbon atoms or of 1 sulphur atom and 0–5 carbon atoms and other combinations known to those in the art. In the "spacer" a carbon atom can appear as a keto group (CO) and a sulphur atom present can appear as a sulphonyl group ($SO_2$). A carbon atom in the "spacer" can be substituted, for example, by hydroxy, carboxy, sulphonyloxy, carbamoyloxy or $C_1$-$C_4$ alkyl such as methyl, ethyl or isopropyl. Examples of "spacers" falling under X include:

—O—, —S—, —NH—, —NH—NH—, —CH$_2$—, —CO—, —CH$_2$O—, —CH$_2$—CH$_2$—, —CH=CH—, —CH$_2$NH—, —S—CH$_2$—, —SO$_2$—CH$_2$—, —O—CH$_2$—, —S—CH$_2$CH$_2$—, —CH$_2$CH$_2$—NH—; —CH$_2$—O—NH—CO—CH$_2$—CH$_2$—, —CHOH—, —CH(COOH)—, —CH(OSO$_3$H)—, —CH(OC-ONH$_2$)—, —CH[CH(CH$_3$)$_2$]—.

Preferred "spacers" are: —CH=CH—, —CH$_2$—, —SCH$_2$—, —NH— and —CH$_2$NH—.

When Y represents the —$SO_2$— group, X can contain neither sulphur nor a carbonyl group as a terminal component. In other words, the —$SO_2$— group cannot be linked directly with a sulphur atom or with a sulphonyl group or a carbonyl group. Examples of "spacers" X which can be linked with Y when it signifies —$SO_2$— include:

—O—,—NH—,—NH—NH—,—CH$_2$—,—CH$_2$O—,—CH$_2$CH$_2$—, —CH=CH—,—CH$_2$NH—,—O—CH$_2$—,—CH$_2$CH$_2$—NH—, —CHOH—,—CH[CH(CH$_3$)$_2$]$_2$].

Preferred "spacers" when Y is —$SO_2$— are: —CH$_2$— and —NH—.

Examples of R groups are:
Phenylcarbamoyl,
p-hydroxy-phenylcarbamoyl,
benzylcarbamoyl,
cyclobutylcarbonyl,
2-(m,p-dihydroxyphenyl)-ethylcarbonyl,
2-phenylglycyl,
2-(o-fluorophenyl)glycyl,
N-phenylglycyl,
α-amino-(2-thienyl)acetyl,
3-(4-imidazolyl)acryloyl,
3-(2-furyl)acryloyl,
3-(2-thienyl)acryloyl,
3-(3-indolyl)acryloyl,
3-(4-hydroxyphenyl)acryloyl,
N-(m-aminophenyl)glycyl,
[(1-methyl-1H-tetrazol-5-yl)thio]acetyl,
[(5-methyl-1,3,4-thiadiazol-2-yl)thio]acetyl,
1H-tetrazol-1-ylacetyl,
[1H-benzotriazol-1-yl)thio]acetyl,
tyrosyl,
2-(p-hydroxyphenyl)glycyl,
2-(m-hydroxyphenyl)glycyl,
2-(m,p-dihydroxyphenyl)glycyl,
tryptophanyl,
t-butoxycarbonyl,
3-pyridylacetyl,
benzyloxycarbonyl,
2-(2-amino-4-thiazolyl)glycyl,
2-amino-4-thiazolglyoxyloyl,
α-hydroxy-phenylacetyl,
α-(sulphonyloxy)-phenylacetyl,
3-α-acetamidocinnamoyl,
2-carboxy-2-(3-thienyl)acetyl,
2-indolylcarbonyl,
2-(R,S)-2-oxo-3-tetrahydrothienyl-carbamoyl,
2-(R)-2-oxo-3-tetrahydrothienyl-carbamoyl,
2-(S)-2-oxo-3-tetrahydrothienyl-carbamoyl.

The compounds of formula I can be divided into two sub-groups, namely into bicyclic compounds having the formula

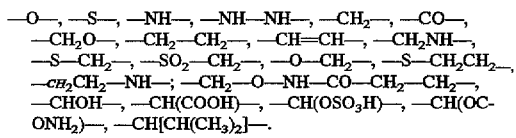

Ia in which R is defined above, $R^{10}$ represents hydrogen, halogen, carbamoyloxy, lower alkanoyloxy or a group of the formula —S—Het, wherein Het represents a 5- or 6-membered heteroaromatic group, and $R^{30}$ represents hydrogen or $R^{10}$ and $R^{30}$ together represent a group having the formula =CH—R$^a$ (c)

wherein R$^a$ signifies one of the groups

—COR$^b$ (c$^1$)

—CH$_2$—OCOR$^c$ (c$^2$)

—CH$_2$—NR$^d$R$^e$ (c$^3$)

—CH$_2$—S—Het (c$^4$)

in which R$^b$ represents alkoxy or amino, R$^c$ represents lower alkyl, phenyl or amino, R$^d$ and R$^e$ each independently represent hydrogen or lower alkyl or R$^d$ and R$^e$ together with the N atom to which they are attached represent a 5- or 6-membered N-heterocycle which optionally contains a further nitrogen, oxygen or sulphur atom and Het represents a 5- or 6-membered heteroaromatic group containing nitrogen, sulphur and/or oxygen, and their pharmaceutically compatible salts, and into tricyclic compounds having the formula

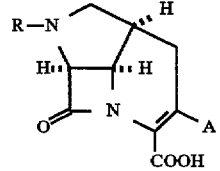

Ib in which R and A are defined above, and their pharmaceutically compatible salts.

The residue which is usable in the 3-position of cephalosporin antibiotics and which is defined as A can represent any of the conventional 3-substituents which are well known to those of ordinary skill in the art of cephalosporin antibiotics, for example, hydrogen, methyl, methoxy, chlorine or a group —CH$_2$L in which L signifies the residue of a nucleophilic compound. As L residues there come into consideration, for example: acetoxy, carbamoyloxy or residues of the formula

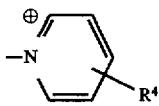

wherein R⁴ represents hydrogen or carbamoyl, or a group —SR⁵ in which R⁵ is an optionally substituted 5- or 6-membered heterocycle with 1–4 hetero atoms, for example, oxygen, sulphur, selenium and/or nitrogen. Tetrazolyl, triazolyl, thia-diazolyl and triazinyl are just some of the many examples of R⁵. These residues can also be substituted, for example, by lower alkyl such as methyl or ethyl, by halogen such as chlorine, fluorine or bromine, by hydroxy or oxo groups. The 1,2,4-triazol-3-yl, 1-methyl-tetrazol-5-yl, 2-methyl-1,3,4-thiadiazol-5-yl, 1,4,5,6-tetrahydro-4-methyl-5,6-dioxo-as-triazin-3-yl, 2,5-dihydro-6-hydroxy-2-methyl-5-oxo-as-triazin-3-yl, 1,2,5,6-tetrahydro-2-methyl-5,6-dioxo-as-triazin-3-yl, and 1,2,5,6-tetrahydro-2-methyl-5,6-dioxo-as-triazin-2-yl groups are examples of such substituted residues. Other examples can be found in *Cephalosporins and Penicillins*, edited by Flynn, Academic Press (1972).

Objects of the present invention are β-lactams of formula I above and pharmaceutically compatible salts thereof and as pharmaceutically active substances, the manufacture of these compounds and intermediates for the manufacture of these compounds, medicaments containing a compound of general formula I or pharmaceutically compatible salts thereof and the manufacture of such medicaments as well as the use of compounds of general formula I and of pharmaceutically compatible salts thereof in the control or prevention of illnesses in mammals, both human and non-human.

Of the compounds of formula I in which R represents lower alkoxycarbonyl there are preferred those in which R represents t-butoxycarbonyl and their pharmaceutically compatible salts. t-Butoxy (1S ,5R)-7-oxo-6-sulpho-2,6-diazabicyclo[3.2.0]heptane-2-carboxylate and (1aS,3aR,6bR)-1,1a3a,6b-tetrahydro-5-methoxy-1-oxo-2,6a-diazacyclobuta[cd]indene-2,6(3H,4H)-dicarboxylic acid 2-t-butyl monoester and their pharmaceutically compatible salts are especially preferred.

Further preferred compounds of formula Ia are:
(1S,5R)-7-Oxo-2-(phenylcarbamoyl)-2,6-diazabicyclo-[3.2.0]heptane-6-sulphonic acid,
(1S ,5R)-2-(benzylcarbamoyl)-7-oxo-6-sulpho-2,6-diazabicyclo[3.2.0]heptane-6-sulphonic acid,
(1S,5R)-7-oxo-2-(N-phenylglycyl)-2,6-diazabicyclo-[3.2.0]heptane-6-sulphonic acid,
(1S,5R)-2-cyclobutylcarbamoyl)-7-oxo-2,6-diazabicyclo-[3.2.0]heptane-6-sulphonic acid,
(1S,5R)-7-oxo-2-(R,S)-(2-oxo-3-tetrahydrothienyl-carbamoyl)-2,6-diazabicyclo[3.2.0]heptane-6-sulphonic acid,
(1S,5R)-7-oxo-2-(R)-(2-oxo-3-tetrahydrothienyl-carbamoyl)-2,6-diazabicyclo[3.2.0]heptane-6-sulphonic acid,
(1S,5R)-2-(4-hydroxy-phenylcarbamoyl)-7-oxo-2,6-diazabicyclo[3.2.0]heptane-6-sulphonic acid,
and their pharmaceutically compatible salts.

Of the compounds of formula I in which R represents the acyl residue of an α-amino acid there are preferred those having the formula

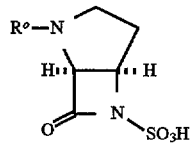

in which R° represents the acyl residue of an α-amino acid having the formula

wherein Q¹ signifies a 5- or 6-membered (hetero)aromatic ring which optionally contains a nitrogen, sulphur and/or oxygen atom and which is optionally bonded with a further fused phenyl ring and n signifies the number 0 or 1, and their pharmaceutically compatible salts. With regard to Q¹, see the discussion hereinabove concerning Q as a 5- or 6-membered (hetero)aromatic ring which optionally contains a nitrogen, sulphur and/or oxygen atom.

Especially preferred groups under group (c) are those of the formula

in which X represents hydrogen, hydroxy or fluorine and m represents the number 1 or 2.

Especially preferred groups Q¹ in groups (c) and, respectively, (c₁) are phenyl, thienyl, p-hydroxyphenyl, m-hydroxyphenyl, m,p-dihydroxyphenyl, o-fluorophenyl, m-fluoro-p-hydroxyphenyl, o-fluoro-p-hydroxyphenyl, indolyl and 2-amino-4-thiazolyl.

Preferred compounds of formula Ic containing group (c) are:
(1S,5R)-7-Oxo-2-L-tyrosyl-2,6-diazabicyclo[3.2.0]heptane-6-sulphonic acid,
(1S,5R)-7-oxo-2-L-tryptophanyl-2,6-diazabicyclo[3.2.0]-heptane-6-sulphonic acid,
(1S,5R)-2-[(R or S)-α-amino-(2-thienyl)acetyl]-7-oxo-2,6-diazabicydo[3.2.0]heptane-6-sulphonic acid,
(1S,5R)-2-[DL-2-(2-amino4-thiazolyl)glycyl]-7-oxo-2,6-diazabicydo[3.2.0]heptane-6-sulphonic acid
and pharmaceutically compatible salts of these compounds.

Especially preferred compounds containing group (c₁) are:
(1S,5R)-7-Oxo-2-(D-2-phenylglycyl)-2,6-diazabicyclo-[3.2.0]heptane-6-sulphonic acid,
(1S ,5R)-7-oxo-2-(L-2-phenylglycyl)-2,6-diazabicyclo-[3.2.0]heptane-6-sulphonic acid,
(1S ,5R)-2-[D-2-(p-hydroxyphenyl)glycyl]-7-oxo-2,6-diazabicyclo[3.2.0]heptane-6-sulphonic acid,
(1S,5R)-2-[R-2-(m-hydroxyphenyl)glycyl]-7-oxo-2,6-diazabicyclo[3.2.0]heptane-6-sulphonic acid,
(1S ,5R)-2-[DL-2-(m-hydroxyphenyl)glycyl]-7-oxo-2,6-diazabicyclo[3.2.0]heptane-6-sulphonic acid,
(1S,5R)-2-[DL-2-(o-fluorophenyl)glycyl]-7-oxo-2,6-diazabicyclo[3.2.0]heptane-6-sulphonic acid,
(1S,5R)-2-[(R,S)-amino-(3,4-dihydroxy-phenyl)acetyl]-7-oxo-2,6-diazabicyclo[3.2.0]heptane-6-sulphonic acid
and pharmaceutically compatible salts of these compounds.

Of the compounds of formula Ia in which R signifies a residue (a) of the formula Q—X—Y— there are preferred those having the formula

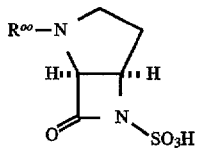

in which $R^{oo}$ represents a group of the formula

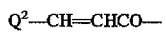  (d)

wherein $Q^2$ signifies a phenyl ring or a 5- or 6-membered heteroaromatic ring which contains nitrogen, sulphur and/or oxygen and which is optionally bonded with an existing phenyl ring,
and their pharmaceutically compatible salts.

Preferred compounds of formula Id containing group (d) are:

(1S,5R)-2-[(E)-3-(2-furyl)acryloyl]-7-oxo-2,6-diazabicyclo [3.2.0]heptane-6-sulphonic acid, (1S,5R)-2-[(E)-3-(3-indolyl)acryloyl]-7-oxo-2,6-diazabicyclo[3.2.0]heptane-6-sulphonic acid, (1S,5R)-2-[(E)-3-(4-imidazolyl)acryloyl]-7-oxo-2,6-diazabicyclo[3.2.0]heptane-6-sulphonic acid, (1S ,5R)-2-[(E)-3-(2-thienyl)acryloyl]-7-oxo-2,6-diazabicyclo[3.2.0]heptane-6-sulphonic acid, (1S ,5R)-(E)-2-[3-(4-hydroxy-phenyl)acryloyl]-7-oxo-2,6-diazabicyclo[3.2.0]heptane-6-sulphonic acid
and their pharmaceutically compatible salts.

Further preferred compounds of formula Ia in which R signifies a residue of the formula Q—X—Y— are compounds having the formula

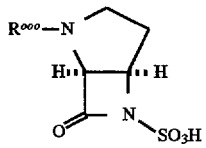

in which $R^{ooo}$ represents a group of the formula

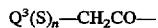  (e)

wherein n signifies 0 or 1 and $Q^3$ signifies a phenyl ring or a 5- or 6-membered N-heterocycle which optionally contains sulphur, which is optionally substituted by lower alkyl or amino and which is optionally bonded with a fused phenyl ring, and their pharmaceutically compatible salts.

Preferred compounds of formula Ie containing group (e) are:

(1S,5R)-2-[[(1-Methyl-1H-tetrazol-5-yl)thio]acetyl]-7-oxo-2,6-diazabicyclo-[3.2.0]heptane-6-sulphonic acid, 1S,5R)-2-[[1H-benzotriazol-1-yl)thio]acetyl]-7-oxo-2,6-diazabicyclo[3.2.0]heptane-6-sulphonic acid, (1S,5R)-2-[[(5-methyl-1,3,4-thiadiazol-2-yl)thio]acetyl]-7-oxo-2,6-diazabicyclo[3.2.0]heptane-6-sulphonic acid, (1S,5R)-7-oxo-2-(1H-tetrazol-1-ylacetyl)-2,6-diazabicyclo [3.2.0]heptane-6-sulphonic acid, (1S,5R)-2-[(2-isopropyl-2H-tetrazol-5-yl)-acetyl]-7-oxo-2, 6-diazabicyclo[3.2.0]heptane-6-sulphonic acid
and their pharmaceutically compatible salts.

The following are further compounds of formula Ia in which R signifies a residue of the formula Q—X—Y—

Benzyl (1S,5R)-7-oxo-6-sulpho-2,6-diazabicyclo[3.2.0]-heptane-2-carboxylate, (1S,5R)-2-[(Z)-3-α-acetamidocinnamoyl]-7-oxo-2,6-diazabicyclo[3.2.0]heptane-6-sulphonic acid, (R/S)-α-(1S ,5R)-2-[2-carboxy-2-(3-thienyl)acetyl]-7-oxo-2,6-diazabicyclo[3.2.0]heptane-6-sulphonic acid, (1S,5R)-7-oxo-2-(3-pyridylacetyl)-2,6-diazabicyclo[3.2.0]-heptane-6-sulphonic acid, (1S ,5R)-2-[(R,S)-2-indolylcarbonyl]-7-oxo-2,6-diazabicyclo[3.2.0]heptane-6-sulphonic acid, (1S ,5R)-2-[(R)-α-hydroxyphenylacetyl]-7-oxo -2,6-diazabicyclo[3.4.0]heptane-6-sulphonic acid, (1S,5R)-2-[(S)-α-hydroxyphenylacetyl]-7-oxo-2,6-diazabicyclo[3.2.0]heptane-6-sulphonic acid, R(α)-[[(1S ,5R)-7-oxo-6-sulfo-2,6-diazabicyclo[3.2.0]hept-2-yl]carbonyl]benzyl sulphate, (1S ,5R)-2-(2-amino-4-thiazolglyoxyloyl)-7-oxo-2,6-diazabicyclo[3.2.0]heptane-6-sulphonic acid
and pharmaceutically compatible salts of these compounds.

The β-lactams of formula I in accordance with the invention as well as their pharmaceutically compatible salts can be manufactured in accordance with the invention by (a) treating a compound having the formula

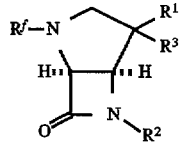  II in which $R^1$, $R^2$ and $R^3$ have the significance given above, with agents yielding the residue R, or (b) for the manufacture of a compound of formula I in which R contains a free amino group or hydroxy group(s), cleaving off the amino protecting group or hydroxy protecting group(s) in a compound having the formula

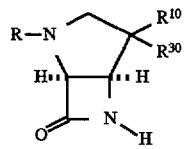  If in which $R^1$, $R^2$ and $R^3$ have the significance given above and $R^f$ represents a residue defined under R having a protected amino group or hydroxy group(s), or (c) for the manufacture of a compound of formula I in which $R^1$ and $R^2$ are different from group (b), treating a compound having the formula

  III in which R has the significance given above, $R^{10}$ represents hydrogen, halogen, carbamoyloxy, lower alkanoyloxy or a group of the formula —S—Het, wherein Het represents a 5- or 6-membered heteroaromatic group, and $R^{30}$ represents hydrogen or $R^{10}$ and $R^{30}$ together represent a group of the formula $=CH-R^a$  (c)

wherein $R^a$ signifies one of the groups

| | |
|---|---|
| —COR$^b$ | (c$^1$) |
| —CH$_2$—OCOR$^c$ | (c$^2$) |
| —CH$_2$—NR$^d$R$^e$ | (c$^3$) |
| —CH$_2$—S≦Het | (c$^4$) | in which $R^b$ represents lower alkoxy or amino, $R^c$ represents lower alkyl or amino, $R^d$ and $R^e$ each represent hydrogen or lower alkyl or $R^d$ and $R^e$ together with the N atom represent a 5- or 6-membered saturated N-heterocycle which optionally contains a further nitrogen, oxygen or sulphur atom and Het represents a 5- or 6-membered heteroaromatic group containing nitrogen, sulphur and/or oxygen,
with an agent yielding the sulpho group —SO$_3$H, or
(d) for the manufacture of a compound of formula I in which $R^1$ and $R^2$ together represent the group (b) defined above, reacting a compound having the formula

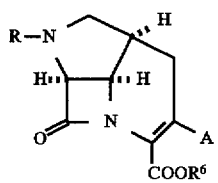

IV in which R and A have the significances given above and $R^6$ represents a carboxylic acid protecting group,
with agent which cleave the carboxylic acid protecting group $R^6$, or
(e) for the manufacture of a pharmaceutically compatible salt of a compound of formula I, converting a compound of formula I into such a salt.

The following procedures can be used for the introduction of the R residue into starting materials of formula II in accordance with variant (a) of the process in accordance with the invention:

(a$^1$) When R contains a terminal carbonyl group or thiocarbonyl group, a compound of formula II is acylated with an acid of the formula ROH or with one of its reactive derivatives. As acylating agents there come into consideration: corresponding acids of the formula ROH in the presence of 2-halopyridinium salts, for example, of 2-chloro- or 2-fluoro-1-methylpyridinium chloride or tosylate, or also in the presence of N,N'-dicylclohexylcarbodimide or carbonyldiimidazole, the latter preferably together with N-hydroxybenztriazole, N-hydroxysuccinimide or N-hydroxyphthalimide. There can also be used corresponding, reactive derivatives of the carboxylic acid such as for example, the acid halide (preferably the chloride), acid anhydride or acid azide. The corresponding thiol esters such as for example, 2-benzthiazolyl thioesters as well as hydroxybenztriazole esters, N-hydroxysuccinimide esters or N-hydroxyphthalimide esters can also be used. The reaction is preferably carried out in an organic solvent or solvent mixture, optionally in admixture with water, for example, acetone, methylene chloride, tetrahydrofuran, dioxan, dimethylacetamide, dimethylformamide or acetonitrile, optionally in admixture with water. The temperature generally lies between –30° C. and room temperature.

(a$^2$) When R contains a terminal sulphonyl group, a compound of formula II is sulphonated with an acid of the formula ROH or with one of its reactive derivatives. Sulphonic acid halides, especially the chlorides, primarily come into consideration as sulphonating agents. In other respects, the reaction is effected essentially as above under (a$^1$).

(a$^3$) When R contains a terminal —CONH— group, a compound of formula II is reacted with a corresponding substituted 3-phenyloxaziridine of the formula

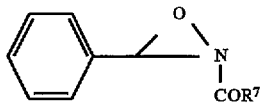

XLV in which $R^7$ represents lower alkoxy or the group Q—X— wherein Q and X have the above significance.
Solvent and temperature range are essentially as above under (a$^1$).

Where the group Q—X— is to be introduced, a starting material of formula XLV in which $R^7$ represents lower alkoxy, especially methoxy, is preferably used. The resulting product of the formula

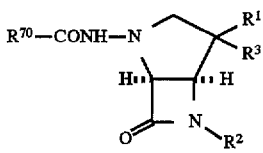

XLVI in which $R^1$, $R^2$ and $R^3$ have the above significance and $R^{70}$ represents lower alkoxy,
is hydrolyzed and decarboxylated with a base, for example, potassium hydroxide in aqueous tetrahydrofuran at room temperature. The resulting intermediate of the formula

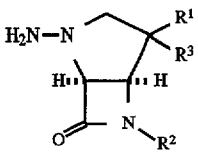

XLVII in which $R^1$, $R^2$ and $R^3$ have the above significance, is acylated with an acid of the formula Q—X—COOH or with one of its reactive derivatives in accordance with the details under (a$^1$) above.

Acids of the formula ROH, which contain amino groups, are preferably protected at the amino group, for example, by benzyloxycrbonyl, t-butoxycarbonyl or chloroacetyl. Corresponding compounds of formula If obtained after the acylation are converted in accordance with the invention according to process variant (b) into end products having a free amino group by cleavage of the amino protecting group. The liberation of the amino group is effected in a manner well known to those of ordinary skill in the art, for example, by hydrogenation with palladium/charcoal or treatment with palladium/charcoal and 1,4-cyclohexadiene in an organic solvent such as ethanol at about 0° to 80° C. (benzyloxycarbonyl); with trifluoroacetic acid, optionally in the presence of anisole, or with hydrogen chloride in an organic solvent such as dioxan at about –20° to 0° C. (t-bubutoxycarbonyl); or with thiourea in a polar solvent, preferably in water at neutral pH, and about 0° to 30° C. (chloroacetyl).

Where a product of formula I in which R contains two vicinal hydroxy groups is to be manufactured, these hydroxy groups in the corresponding starting material of the formula ROH can be protected; the hydroxy groups are liberated after the reaction has been carried out:

Preferred protection is by diphenylmethyl (for example a 3,4-dihydroxyphenyl group is then converted into the 2,2- diphenyl-1,3-benzodioxol-5-yl group) by heating with diphenyldichloromethane. The cleavage of the diphenylmethyl group is preferably effected by the action of an acidic agent in a trace of water, for example, by concentrated aqueous hydrochloric acid or, especially, by trifluoroacetic acid with a trace of water. The reaction temperature is suitably 0° C. to about room temperature. If desired, this cleavage can also be carried out by hydrogenation with palladium-charcoal in an inert organic solvent, for example, methanol, ethanol, tetrahydrofuran or ethyl acetate, at a temperature between about 0° C. and 80° C.

The hydroxy groups can also be protected by lower alkanoyl groups, for example, acetyl. Introduction is for example, by treatment with a lower alkanoyl halide or anhydride, for example, the chloride, in the presence of a base such as sodium hydroxide, DBU or diisopropylethylamine. The cleavage is effected under mild alkaline conditions (pH about 7–8), for example, with sodium hydroxide or carbonate, at about 0° C. to 50° C.

A further possibility of protecting the hydroxy groups is the use of silyl groups, for example, trimethyisilyl and t-butyldimethylsilyl. These are advantageously introduced by treatment with the corresponding silyl chloride. The cleavage can be effected by the action of a fluoride, preferably tetrabutylammonium fluoride, in an organic solvent, for example, acetonitrile, at about 0° C. to 50° C.

According to variant (c) of the process in accordance with the invention a compound III is sulphonated. The sulphonation can be effected in a manner known per se by reaction with sulphur trioxide or a reactive derivative thereof, for example, with complexes of sulphur trioxide and an organic base such as pyridine, dimethylformamide, picoline etc. The reaction is effected for example, at about –20° to +80° C. in an inert organic solvent, for example, in an ether such as dioxan, in an ester such as ethyl acetate, in a chlorinated hydrocarbon such as methylene chloride; in acetonitrile, dimethylformamide or pyridine.

Ester protecting groups of the esters of formula IV used according to variant (d) of the process in accordance with the invention are preferably those which can be transformed into the free carboxy group under mild conditions, for example, t-butyl, p-nitro-benzyl, benzyl, benzhydryl, allyl, etc. The ester protecting groups are cleaved off for example, as follows: benzyl and p-nitrobenzyl by hydrogenation over palladium/charcoal at about 0° C. to 80° C. in an organic solvent such as ethyl acetate or methanol or in water or by hydrolysis in the presence of sodium sulphide at (or below) 0° C. to room temperature in a solvent such as for example, dimethylformamide (preferably aqueous); t-butyl by treatment with aqueous hydrochloric acid or by reaction with trifluoroacetic acid in the presence of anisole at about 0° C. to room temperature with or without additional solvent such as for example, methylene chloride; allyl by palladium-(O)-catalyzed transallylation in the presence of the sodium or potassium salt of 2-ethylcaproic acid, see for example, *J. Org. Chem.*, 1982, 47, 587.

The following Reaction Schemes I–IV illustrate the process for the manufacture of the products in accordance with the invention and, respectively, of the intermediates which occur in the syntheses.

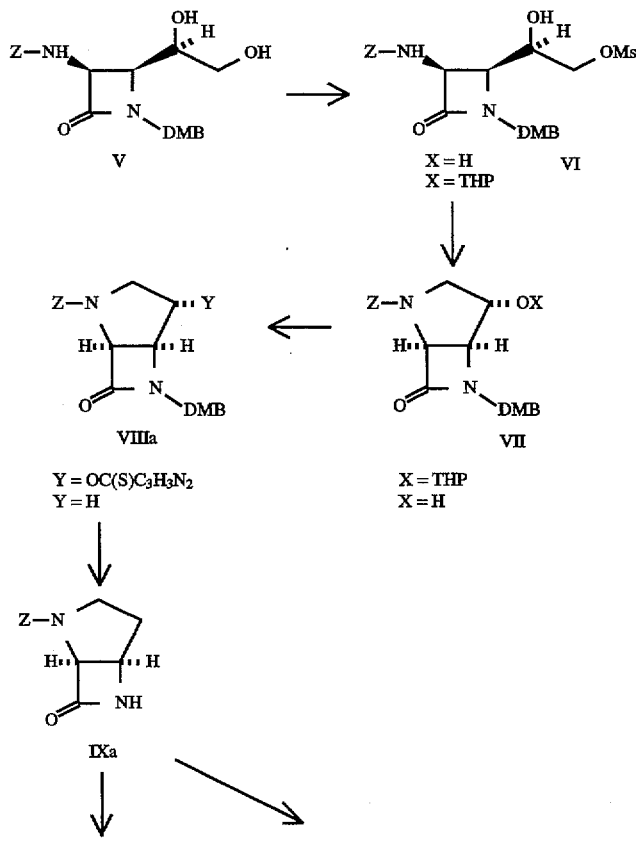

Scheme I

-continued
Scheme I
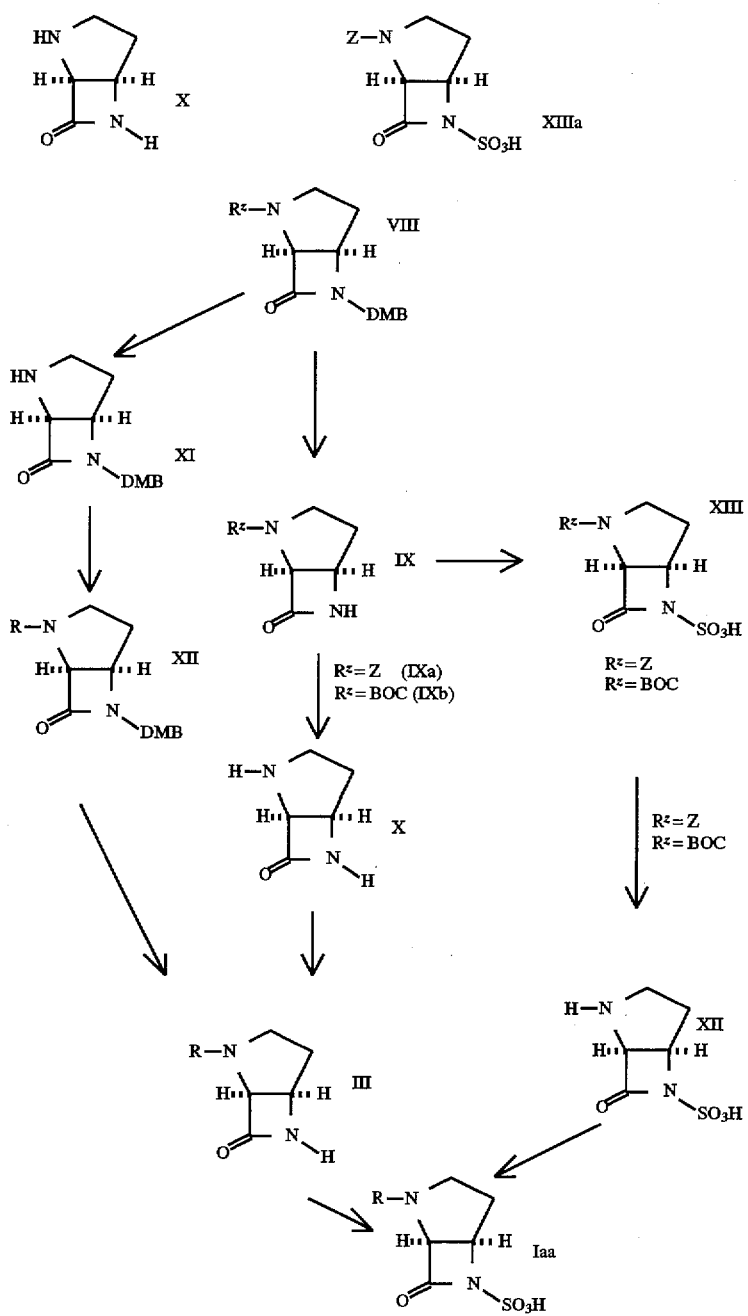
Scheme II
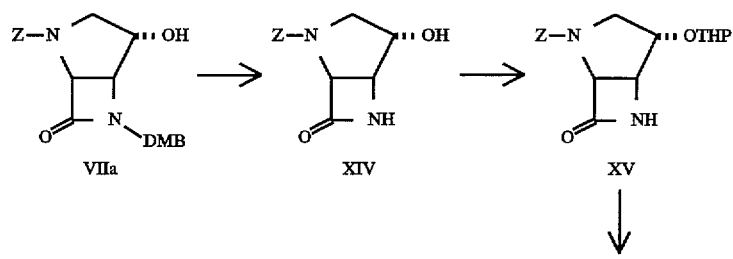

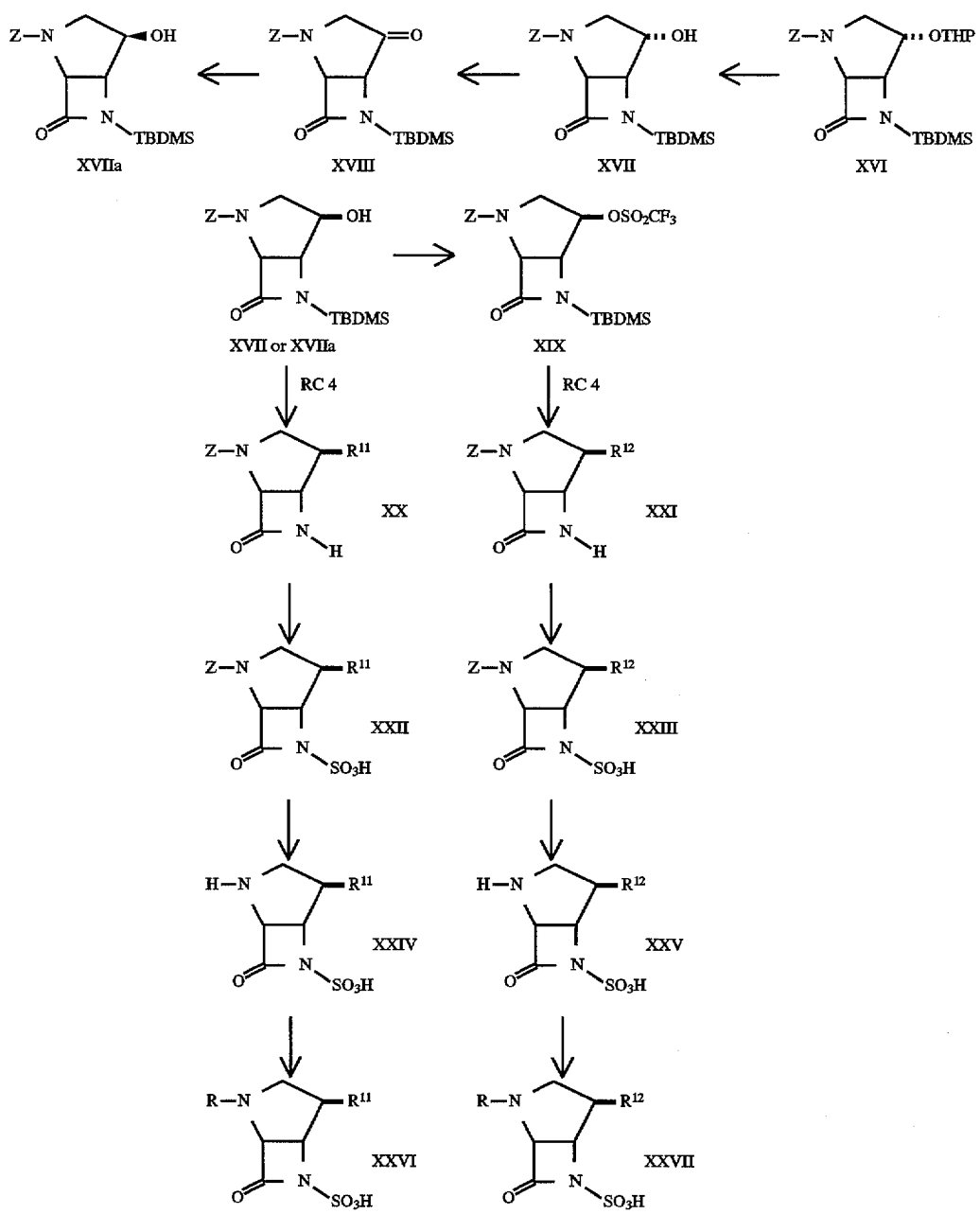
-continued
Scheme II
Scheme III
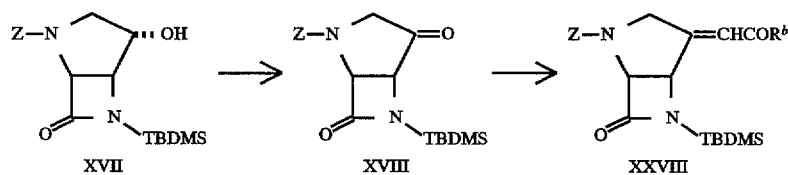

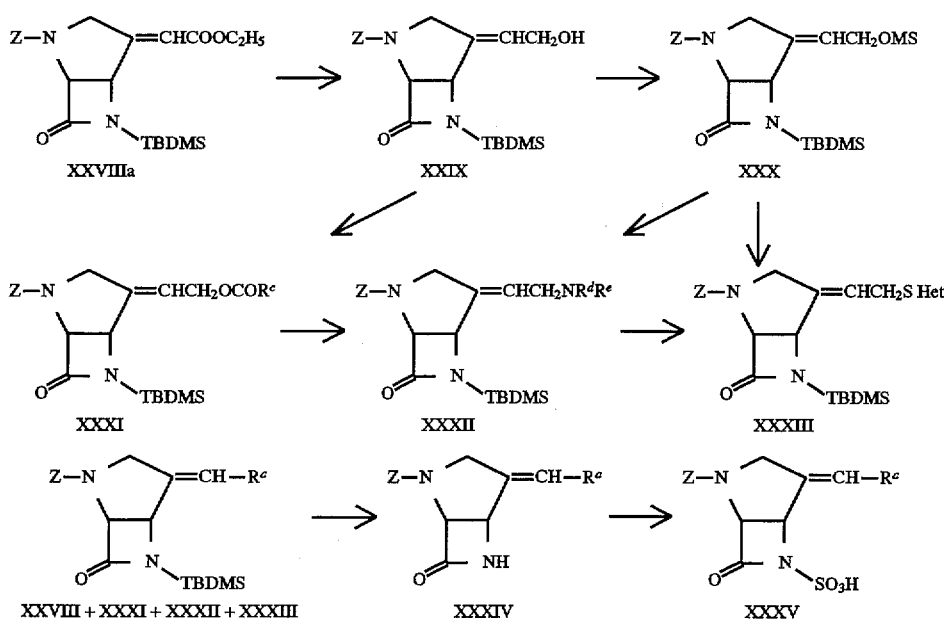
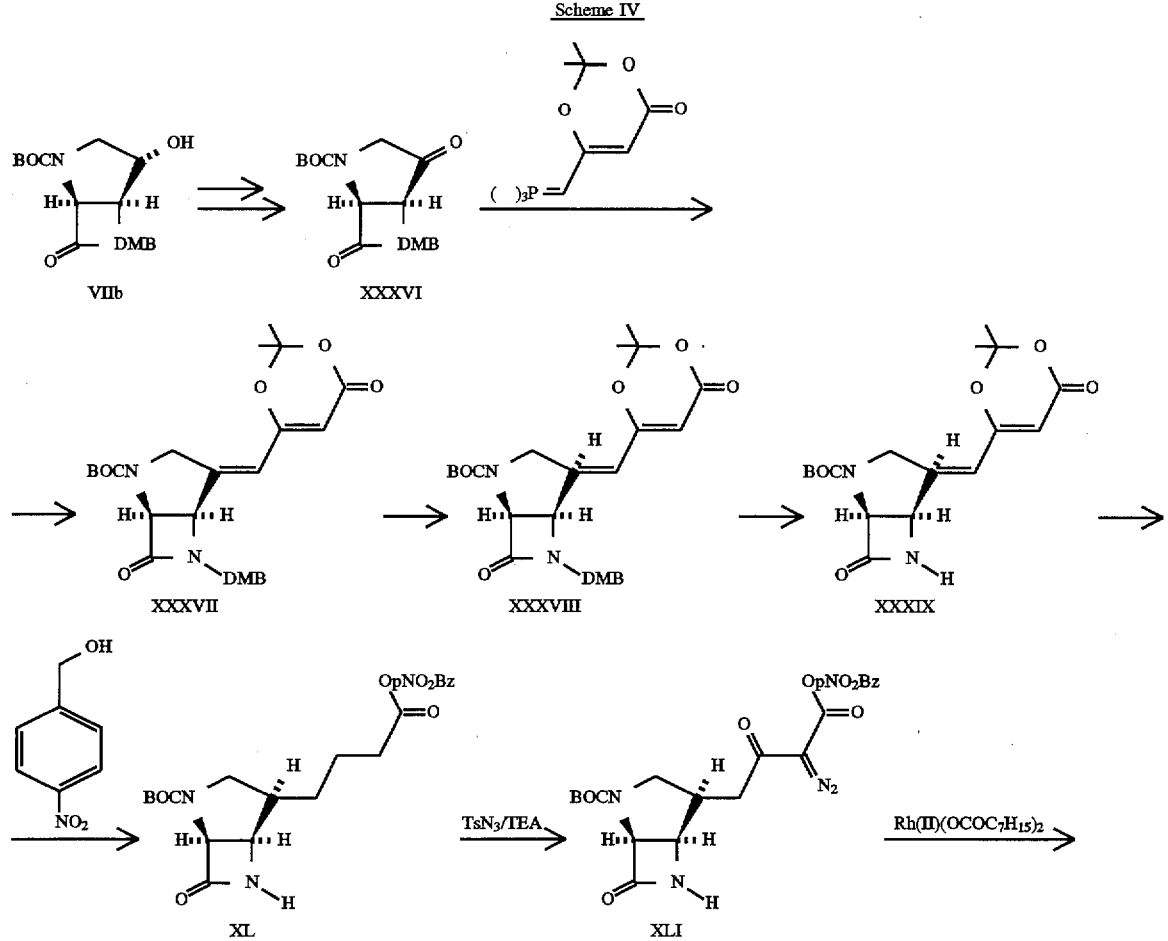

-continued
Scheme IV

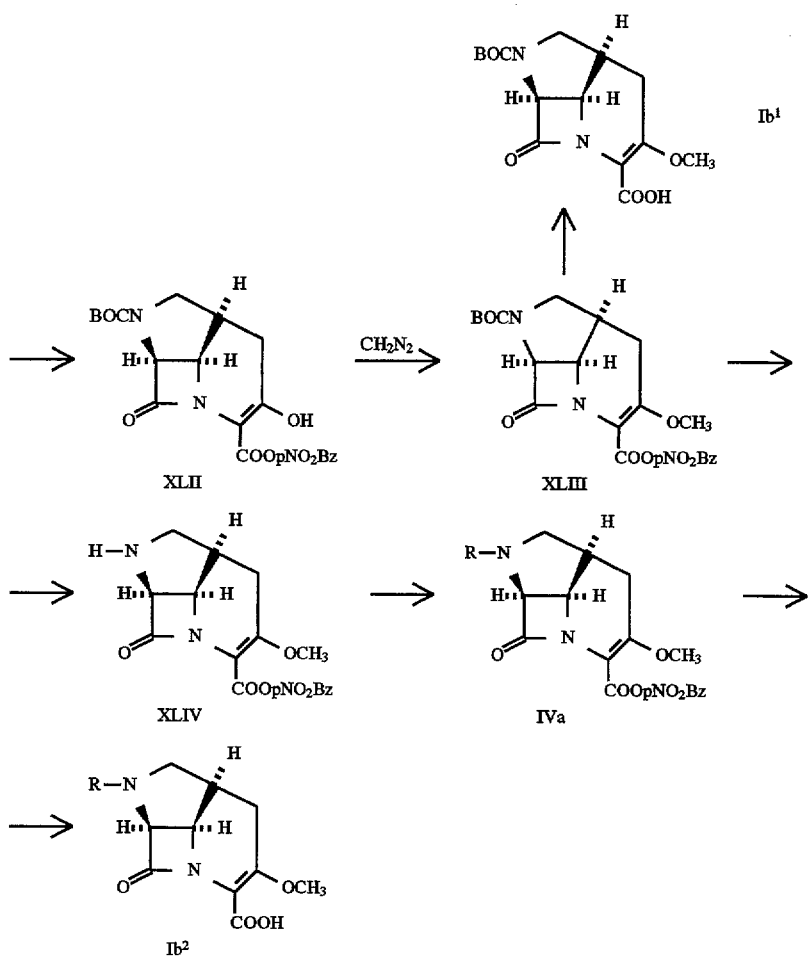

The symbols in Schemes I through IV have the following significances:
X=hydrogen or tetrahydropyranyl
THP=tetrahydropyranyl
Ms=methanesulphonyl
Y=hydrogen or [(1-imidazolyl)thiocarbonyl]oxy
$R^z$=benzyloxycarbonyl or t-butoxycarbonyl
Z=benzyloxycarbonyl
BOC=t-butoxycarbonyl
Ø=phenyl
R, $R^a$, $R^b$, $R^c$, $R^d$, $R^e$=the meaning given above in formula I
DMB=3,4-dimethoxybenzyl or 2,4-dimethoxybenzyl
p$NO_2$Bz=p-nitrobenzyl
TBDMS=t-butyl-dimethylsilanyl
KW4=reversal of configuration in the 4-position (see hereinafter)
$R^{11}$=carbamoyloxy or lower alkanoyloxy
$R^{12}$=Hal, —S—Het (Het has the above significance).

Scheme I describes the preparation of compounds VIII with $R^z$=benzyloxycarbonyl (=compounds VIIIa). The preparation of compounds VIII with $R^z$=t-butoxycarbonyl proceeds in exactly the same manner.

Further details concerning the preparation of starting materials II, If, III and IV used in accordance with the invention will be evident from the following working Examples. In Scheme II the intermediate XVIIa can be prepared with sodium borohydride in analogy to Example 16. For brevity, formulae XIX–XXVI have been drawn with a solid line (—) in the 4-position, with the corresponding isomer being obtained depending on whether the 4(S)-hydroxy compound XVII or the 4(R)-hydroxy compound XVIIa has been used, whereby the intermediates XX and XXI with a reversal of configuration in the 4-position result (denoted by "RC 4" in Scheme II). For the rest, the intermediates XX are prepared for example, by reaction with an isocyanate, for example, chloroacetyl isocyanate, followed by cleavage of the chloroacetyl group with a base such as potassium hydroxide ($R^{11}$=carbamoyloxy) or by reaction with the corresponding anhydride such as acetic anhydride ($R^{11}$=lower alkanoyloxy).

In Scheme III the intermediate XXIX can be prepared by treating the ester XXVIIIa with sodium borohydride. The product XXIX can be reacted with for example, mesyl chloride, whereby the product XXX results. By reacting the product XXIX with a lower alkanoyl chloride or an isocyanate (for example, chloroacetyl isocyanate), followed by cleavage of the chloroacetyl group with a base there are obtained products XXXI, and by reacting product XXX with the corresponding. amine or heterocyclic thiol in the presence of a base there result products XXXII and, respectively, XXXIII. The products XXVIII, XXXI, XXXII and XXXIII can all be converted into corresponding end products XXXV by cleavage of the 6-protecting group and sulphonylation. The group Z cannot be removed without saturating the double bond in the 4-position and, therefore, when an end product having another residue R in position 2 is desired, the corresponding 2-BOC-protected compound (obtainable for example, by removing Z by hydrogenation and reaction with t-butoxycarbonyl anhydride) need be used in place of the Z-protected intermediate XVII.

As mentioned earlier, the compounds of general formula I in accordance with the invention and pharmaceutically compatible salts thereof with bases exhibit pronounced β-lactamase-inhibiting activities against β-lactamases from various bacterial strains as found in mammals. As illustrated hereinafter, these therapeutically valuable properties can be determined in vitro on isolated β-lactamases:

A. Isolation of the β-lactamases

Various β-lactamases can be isolated from penicillin- or cephalosporin-resistant bacterial strains such as *Klebsiella pneumoniae* NCTC 418, *Proteus vulgaris* 1028, *Bacillus licheniformis* 749/C, *Escherichia coli* SN01 and *Citrobacter freundii* 1203. For this purpose, the corresponding strains are cultivated in Tryptic Soy Broth (Difco) and harvested by centrifugation in the last logarithmic growth phase (when necessary 50–100mg/l of ampicillin are added to the medium towards the end of the log-phase in order to induce the β-lactamase). The thus-obtained bacterial mass is treated with 20 mM Tris-HCl buffer (pH 7.0); the cells are broken open with a French press while cooling. The mixture is centrifuged (20,000 r/min.) for 20–30 minutes and a clear crude extract is obtained. The purification of the proteins is effected according to the methods of Cartwright, S. J. & Waley, S. G. [*Biochem. J.* 221, 505–512 (1980)] and, for *B. licheniformis*, Ellerby, L. M. et al. [*Biochemistry*, 29, 5797–5806 (1990)].

B. Determination of the β-lactamase activity

The determination of the activity of the isolated β-lactamases can be carried out according to the method of O'Callaghan, C. H. et al. [*Antimicr. Ag. Chemother.*, 1, 283–288 (1972)] using the chromogenic cephalosporin nitrocefin (87/312 from Glaxo). The requisite test batch contains per ml of water: 50 mM phosphate buffer (pH 7.0), 0.1 mM nitrocefin and sufficient enzyme (β-lactamase) to achieve a αA/min. of about 0.1. The cleavage of the substrate, which is accompanied by a change in colour, is effected at 37° C. and is followed quantitatively at 482 nm using a spectral photometer.

C. Determination of the β-lactamase-inhibiting activity of the compounds of general formula I The above-described cleavage of the chromogenic substrate by β-lactamases (test B.) can be inhibited by the addition of compounds of general formula I (inhibitors). Since it has been found that the inhibitors irreversibly inactivate the β-lactamase in a time-dependent reaction, the reaction (cleavage of the substrate) is in each case started by addition of the substrate after a pre-incubation period of β-lactamase with inhibitor of 15 minutes. As a measurement for the affinity of the particular tested inhibitor to the β-lactamase, which is a measurement of the strength of the inhibitor, there serves that concentration which inhibits by 50% (IC 50 in nM) the cleavage of the substrate (nitrocefin) effected under the above test conditions (test B) in the absence of an inhibitor. 4 to 6 tests with different concentrations of inhibitor were carried out in order to determine the IC 50. The determination of the IC 50 was effected by means of a graph.

The results obtained in the above test (test C) are presented in Table 1 hereinafter.

TABLE 1

(Test organism: *Citrobacter freundii*)
The IC 50 value in nM is given for the end products of the following working Examples. This is a measurement of the β-lactamase inhibition. An IC 50 value of 1000 nM or less is considered to be significant.

| Example No. | IC 50 nM | Example No. | IC 50 nM |
|---|---|---|---|
| 1(a) | 100 | 15 | 630 |
| 1(b) | 225 | 16(a) | 14 |
| 2 | 220 | 16(b) | 334 |
| 3 | 330 | 17(a) | 156 |
| 4(b) | 250 | 17(b) | 285 |
| 4(d) | 275 | 17(c) | 400 |
| 4(f) | 280 | 17(d) | 197 |
| 4(g) | 390 | 17(e) | 250 |
| 5(a) | 85 | 17(f) | 193 |
| 5(b) | 110 | 17(g) | 427 |
| 5(e) | 85 | 17(h) | 145 |
| 5(g) | 150 | 17(i) | 245 |
| 5(i) | 115 | 17(j) | 79 |
| 5(j) | 23 | 17(k) | 109 |
| 5(k) | 73 | 17(l) | 437 |
| 5(l) | 860 | 17(m) | 359 |
| 5(m) | 24 | 17(n) | 272 |
| 5(n) | 67 | 17(p) | 383 |
| 5(p) | 178 | 17(q) | 576 |
| 5(q) | 5 | 17(r) | 490 |
| 6(b) | 310 | 17(s) | 38 |
| 6(d) | 500 | 17(t) | 53 |
| 6(e) | 465 | 17(u) | 62 |
| 6(f) | 11 | 17(v) | 200 |
| 6(h) | 6 | 17(w) | 109 |
| 6(i) | 700 | 17(x) | 199 |
| 6(j) | 280 | 17(y) | 238 |
| 6(o) | 350 | 17(z) | 98 |
| 6(p) | 56 | 17(aa) | 75 |
| 6(q) | 375 | 17(ab) | 194 |
| 6(s) | 584 | 17(ac) | 70 |
| 6(t) | 12 | 17(ad) | 75 |
| 6(u) | 40 | 17(ae) | 200 |
| 6(v) | 3.5 | 17(af) | 107 |
| 6(w) | 22 | 17(ag) | 337 |
| 7 | 505 | 19 | 430 |
| 8(a) | 75 | 20 | 165 |
| 8(b) | 500 | 21 | 695 |
| 8(c) | 120 | 22 | 220 |
| 8(d) | 34 | 23(a) | 97 |
| 11(a) | 76 | 23(b) | 50 |
| 11(b) | 573 | 23(c) | 420 |
| 11(c) | 1 | 23(d) | 283 |
| 11(d) | 142 | 23(e) | 138 |
| 12(a) | 105 | 23(f) | 30 |
| 12(b) | 115 | 23(g) | 280 |
| 13 | 63 | 23(h) | 920 |
| 14(a) | 32 | 23(i) | 70 |
| 14(b) | 65 | 23(j) | 38 |
| 14(c) | 826 | 23(k) | 273 |
|  |  | 23(l) | 5 |

D. Determination of the β-lactamase-inhibiting activity by combination of a compound of general formula I with ceftriaxone The minimum inhibitory concentration in vitro (MIC in μg/ml) of a 1:4 combination of ceftriaxone with a compound of formula I against *Citrobacter freundii* is measured and compiled in Table 2 hereinafter.

TABLE 2

| Example No. | MIC μg/ml | Example No. | MIC μg/ml |
|---|---|---|---|
| 1(a) | 8 | 12(a) | 4 |
| 1(b) | 8 | 12(b) | 2 |
| 2 | 2 | 13 | 4 |
| 3 | 2 | 17(a) | 2 |

TABLE 2-continued

| Example No. | MIC µg/ml | Example No. | MIC µg/ml |
| --- | --- | --- | --- |
| 4(b) | 2 | 17(b) | 2 |
| 4(d) | 2 | 17(c) | 2 |
| 4(f) | 4 | 17(d) | 2 |
| 4(i) | 8 | 17(e) | 2 |
| 5(a) | 4 | 17(f) | 2 |
| 5(b) | 2 | 17(g) | 2 |
| 5(e) | 2 | 17(j) | 2 |
| 5(f) | 16 | 17(k) | 16 |
| 5(g) | 8 | 17(l) | 4 |
| 5(h) | 4 | 17(m) | 16 |
| 5(i) | 2 | 17(n) | 16 |
| 5(j) | 0.5 | 17(u) | 2 |
| 5(k) | 2 | 17(w) |  |
| 5(l) | 4 | 17(x) | 2 |
| 5(m) | 0.5 | 17(y) | 1 |
| 5(p) | 1 | 17(z) | 1 |
| 5(q) | 2 | 17(aa) | 0.5 |
| 6(b) | 4 | 17(ab) | 1 |
| 6(d) | 2 | 17(ac) | 1 |
| 6(e) | 4 | 17(ad) | 2 |
| 6(f) | 4 | 17(ae) | 1 |
| 6(h) | 1 | 17(af) | 1 |
| 6(i) | 4 | 17(ag) | 1 |
| 6(k) | 8 | 18 | 1 |
| 6(l) | 8 | 19 | 2 |
| 6(o) | 2 | 20 | 4 |
| 6(p) | 2 | 21 | 4 |
| 6(q) | 2 | 23(a) | 16 |
| 6(r) | 2 | 23(b) | 0.5 |
| 6(s) | 4 | 23(c) | 8 |
| 6(u) | 2 | 23(d) | 1 |
| 6(v) | 8 | 23(e) | 1 |
| 6(w) |  | 23(f) | 0.5 |
| 7 | 4 | 23(g) | 2 |
| 8(a) | 4 | 23(h) | 16 |
| 8(b) | 1 | 23(i) | 1 |
| 8(c) | 2 | 23(j) | 1 |
| 8(d) | 0.5 | 23(k) | 2 |
| 11(a) | 8 | 23(l) | 2 |
| 11(b) | 16 |  |  |
| 11(c) | 16 | Ceftriaxone alone control | 128 |
| 11(d) | 4 |  |  |

The products in accordance with the invention can be used as medicaments, for example, in the form of pharmaceutical preparations which contain them or their salts in admixture with a pharmaceutical, organic or inorganic inert carrier material which is suitable for parenteral or enteral administration, such as for example, water, gelatine, gum arabic, lactose, starch, magnesium stearate, talc, vegetable oils, polyalkylene glycols, Vaseline, etc. The pharmaceutical preparations can be present in solid unit dosage form, for example, as tablets, dragees, suppositories, capsules; or in liquid unit dosage form, for example, as solutions, suspensions or emulsions. They may be sterilized and/or may contain adjuvants such as preserving, stabilizing, wetting or emulsifying agents, salts for varying the osmotic pressure, anaesthetics or buffers, the types and the use of which are well known to those of ordinary skill in the art. The compounds of formula Ia and their salts preferably come into consideration for parenteral administration and, for this purpose, are preferably prepared as lyophilizates or dry powders for dilution with usual agents such as water or isotonic saline. The compounds of formula Ib and their salts as well as the compounds of formula Ic in which $R^o$ represents group ($c^1$) come into consideration for parenteral administration and also for enteral administration in the appropriate unit dosage forms well known in the art.

As mentioned earlier, the compounds of formula I and their pharmaceutically compatible salts can be used in accordance with the invention in the control or prevention of illnesses in mammals, human and non-human, especially in the control of β-lactamase-forming pathogens in combination with β-lactam antibiotics, that is antibiotics which contain a β-lactam ring, for example penicillins such as benzylpenicillin, piperacillin, phenoxymethylpenicillin, carbenicillin, methicillin, propicillin, tricarcillin, ampicillin, amoxycillin or mecillinam and cephalosporins such as ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R,7R)-7-[(Z)-2-(2-amino-4-thiazolyl)-2-(methoxyimino)acetamido]-3-(azidomethyl)-8oxo-5-thia-1-azabicyclo[4.2.0]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.01oct-2-ene-2-carboxylate. Thereby, the compounds of formula I or pharmaceutically compatible salts thereof with bases can be administered before, simultaneously with or after the administration or intake of β-lactam antibiotics. Where the products in accordance with the invention are administered simultaneously with a β-lactam antibiotic, then this can be effected by administration as an ad-hoc combination or in the form of a pharmaceutical combination which contains a compound of formula I or a pharmaceutically compatible salt thereof with a base and a β-lactam antibiotic; such pharmaceutical combinations are also an object of the present invention.

The dosage of the compounds of formula I and of the pharmaceutically compatible salts thereof with bases can vary within wide limits and will, of course, be fitted in each particular case to the individual requirements and to the β-lactamase-producing pathogen to be controlled. In general, a daily dosage of about 0.1 to about 2.0 g should be appropriate. The ratio of β-lactamase inhibitor (compound of formula I or pharmaceutically compatible salt thereof with a base) to β-lactam antibiotic can also vary within wide limits and will be fitted to the individual requirements in each particular case. In general, a ratio of about 1:20 to about 1:1 should be appropriate.

As mentioned earlier, medicaments. containing a compound of formula I or a pharmaceutically compatible salt thereof are also an object of the present invention, furthermore also a process for the manufacture of such medicaments which is characterized by bringing one or more compounds of formula I or pharmaceutically compatible salts thereof and, if desired, one or more other therapeutically valuable substances into a galenical administration form; in this conection reference is again made to the pharmaceutical combinations referred to above, which are also an object of the present invention. In particular, pharmaceutical combinations containing a compound of formula I or a pharmaceutically compatible salt thereof and a β-lactam antibiotic, for example, a penicillin such as benzylpenicillin, piperacillin, phenoxymethylpenicillin, carbenicillin, methicillin, propicillin, tricarcillin, ampicillin, amoxycillin or mecillinam or a cephalosporin such as ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R,7R)-7-[(Z)-2-(2-amino-4-thiazolyl)-2-(methoxyimino)-acetamido]-3-(azidomethyl)-8-oxo-5-thia-1-azabicyclo[4.2.01]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-

(azidomethyl)-8-oxo-5-thia-1-azabicyclo[4.2.0]oct-2-ene-2-carboxylate, are an object of the present invention. Such combinations are suitable for the control of β-lactamase-forming pathogens.

The following abbreviations are used in the Examples hereinafter, which illustrate the present invention in more detail, but are not intended to limit its extent in any manner: DMF signifies dimethylformamide, THF signifies tetrahydrofuran, AIBN signifies α,α'-azo-isobutyronitrile, DCC signifies dicyclohexyl-carbodiimide, HOBT signifies 1-hydroxybenzotriazole and DMSO signifies dimethyl sulphoxide. All temperatures are in degrees Celcius unless otherwise stated.

EXAMPLE 1

(a) Benzyl (1S,5R)-7-oxo-6-sulpho-2,6-diazabicyclo[3.2.0]-heptane-2-carboxylate sodium salt 343mg (1.39 mmol) of benzyl (1S,5R)-7-oxo-2,6-diazabicyclo[3.2.0]heptane-2-carboxylate were dissolved in a mixture of 5 ml of methylene chloride and 2.5 ml DMF and treated dropwise while cooling with ice with 341 mg (2.22 mmol) of DMF-SO$_3$ complex dissolved in 1 ml of DMF. After 1.5 hours the mixture was adjusted to pH 7 with saturated, aqueous sodium hydrogen carbonate solution while cooling. The mixture was treated with a small amount of water, the phases were separated and the aqueous phase was extracted twice with about 5 ml of methylene chloride. The aqueous phase was concentrated by evaporation and fractionated over a polymeric hydrophobic gel (75–150µ) with water as the eluent. The fractions which contain the product were combined and lyophilized.

Yield: 330 mg (68%) of colourless powder

IR (KBr): 1759, 1707 cm$^{-1}$

Elementary analysis: $C_{13}H_{13}N_2O_6SNa$ Calc. C 44.83 H 3.76 N 8.04 S 9.20 Found C 44.52 H 3.85 N 7.94 S 8.95

The benzyl (1S,5R)-7-oxo-2,6-diazabicyclo[3.2.0]heptane-2-carboxylate used as the starting material was prepared as follows:

Benzyl (2S,3S)-1-(3,4-dimethoxybenzyl)-2-[(R)-1-hydroxy-2-[(methylsulphonyl)oxy]ethyl]-4-oxo-3-azeiidinecarbamate The reaction mixture from 215 g (0.5 m01) of benzyl (2S,3S)-1-(3,4-dimethoxybenzyl)-2-[1(R),2-dihydroxyethyl]-4-oxo-3-azetidinecarbamate (European Patent Publication No. 73061) and 84 ml (0.6 mol) of triethylamine in 5.21 of THF was warmed to 40°–45° C. until all diol was dissolved. Thereto there were added dropwise within 75 minutes 47 ml (0.6 mol) of mesyl chloride and the mixture was left to stir for a further 30 minutes before the warm, slightly turbid reaction mixture was filtered. The product crystallizes from the filtrate overnight in a refrigerator and it was filtered off under suction and rinsed with 3×100 ml of THF. About a further 10% of product was obtained after concentration of the mother liquor.

Yield: 244 g (96%)

M.p.: 158° C. (ethanol/water)

Elementary analysis: $C_{23}H_{28}N_2O_9S$ Calc. C 54.32 H 5.55 N 5.51 S 6.30 Found. C 54.32 H 5.34 N 5.57 S 6.35

Benzyl (2S,3S)-1-(3,4-dimethoxybenzyl)-4-oxo-2-[(R)-2-[(methylsulphonyl)oxy]-1-[[(R,S)-tetrahydro-2H-pyran-2-yl]oxy]ethyl]-3-azetidinecarbamate 53 ml (0.58 mol) of dihydropyran dissolved in 150 ml of methylene chloride were added dropwise at 12° C. to a solution of 244 g (0.48 mol) of benzyl (2S,3S)-1-(3,4-dimethoxybenzyl)-2-[(R)-1-hydroxy-2-[(methylsulphonyl)oxy]ethyl]-4-oxo-3-azeti-dinecarbamate and 48 g (0.19 mol) of pyridinium p-toluene-sulphonate in 5.5 liters of methylene chloride. The mixture was stirred at room temperature overnight, thereafter extracted with 2×1000 ml of water, the organic phase was dried over magnesium sulphate and concentrated. A yellowish oil remained behind.

Yield: 267 g (94%)

IR (film): 1760, 721 cm$^{-1}$

MS: (M+H—DHP)$^+$509

Benzyl (1S,4S ,5S)-6-(3,4-dimethoxybenzyl)-7-oxo-4-[[(R,S)-tetrahydro-2H-pyran-2-yl]oxy]-2,6-diazabicyclo[3.2.0]heptane-2-carboxylate A solution of 267 g (0.45 mol) of benzyl (2S,3S)-1-(3,4-dimethoxybenzyl)-4-oxo-2-[(R)-2-[(methylsulphonyl)oxy]-1-[[(R,S)-tetrahydro-2H-pyran-2-yl]oxy]-ethyl]-3-azetidinecarbamate in 5 liters of THF was cooled to 12° C. and treated portionwise with 18 g (0.45 mol) of sodium hydride (60% suspension in oil). The mixture was left to stir at room temperature for a further 3 hours and was subsequently treated with 2 liters of water and 5 liters of ether. After separating the phases the aqueous phase was extracted once with 500 ml of ether, the combined organic phases were washed once with 1.5 liters of saturated, aqueous sodium chloride solution and dried over magnesium sulphate. After concentration there were obtained 225 g of a yellow turbid oil which still contained about 7 g of mineral oil from the sodium hydride suspension. It was processed without further purification.

Yield: 218 g (98%)

IR (film): 1772, 1708 cm$^{-1}$

MS: (M+H)$^+$497

Benzyl (1S,4S,5S)-6-(3,4-dimethoxybenzyl)-4-hydroxy-7-oxo-2,6-diazabicyclo[3.2.0]heptane-2-carboxylate The benzyl (1S,4S,5S)-6-(3,4-dimethoxybenzyl)-7-oxo-4-[[(R,S)-tetrahydro-2H-pyran-2-yl]oxy]-2,6-diazabicyclo[3.2.0]-heptane-2-carboxylate (218 g, 0.44 mol), still contaminated with mineral oil, were dissolved in 5.5 liters of methanol, treated with 14 g (56 mmol) of pyridinium p-toluenesulphonate and stirred at 53° C. overnight. Thereafter, the reaction solution was concentrated and chromatographed over 1150 g of silica gel (0.065–0.2 mm particle size) with ethyl acetate. The thus-obtained pure oil can be crystallized from isopropanol or processed directly.

Yield: 166 g (92%)

M.p.: 100°–102° C. (isopropanol)

Elementary analysis: $C_{22}H_{24}N_2O_6$ Calc. C 64.07 H 5.87 N 6.79 Found C 64.00 H 5.80 N 6.80

Benzyl (1S,4S,5S)-6-(3,4-dimethoxybenzyl)-7-oxo-4-[[(1-imidazoly)thiocarbonyl]oxy]-2,6-diazbicyclo[3.2.0]heptane-2-carboxylate 166 g (0.4 mol) of benzyl (1S,4S,5S)-6-(3,4-dimethoxybenzyl)-4-hydroxy-7-oxo-2,6-diazabicyclo[3.2.0]heptane-1-carboxylate and 144 g (0.8 mol) of 1,1'-thiocarbonyldiimidazole were dissolved in 1.31 of THF and heated to boiling under reflux overnight. Subsequently, the solvent was removed under reduced pressure and the dark brown oil was separated by chromatography over 1200 g of silica gel (0.063–0.2 mm particle size) with ethyl acetate: hexane 2:1.

Yield: 200 g (95%) of orange coloured oil
IR (film): 1766, 1709 cm$^{-1}$
MS (M+H+1-thioglycerol)$^+$: 631

Benzyl (1S,5R)-6-(3,4-dimethoxybenzyl)-7-oxo-2,6-diazabicyclo[3.2.0]heptane-2-carboxylate 200 g (0.38 mol) of benzyl (1S,4S,5S)-6-(3,4-dimethoxybenzyl)-7-oxo-4-[[(1-imidazolyl)thiocarbonyl]oxy]-2,6-diazabicyclo[3.2.0]heptane-2-carboxylate were heated to 80° C. in 4.2liters of toluene. A solution of 213 ml (0.8 mol) of tributyltin hydride and 6.9 g (0.04 mol) of AIBN in 320 ml of toluene were added dropwise thereto while stirring. After completion of the dropwise addition the mixture was stirred at this temperature for a further 45 minutes before the solvent was removed under reduced pressure. There remained behind a yellowish turbid oil which was chromatographed over 1100 g of silica gel (0.063–0.2 mm particle size with 1) ethyl acetate: hexane 1:10; 2) ethyl acetate: hexane 2:1.

Yield: 135 g (90%) of colourless oil
IR(film): 1755, 1705 cm$^{-1}$
MS (EI): (M-dimethoxybenzyl isocyanate) 203

Benzyl (1S,5R)-7-oxo-2,6-diazabicyclo[3.2.0]heptane-2-carboxylate 135 g (0.34 mol) of benzyl (1S,5R)-6-(3,4-dimethoxybenzyl)-7-oxo-2,6-diazabicyclo[3.2.0]heptane-2-carboxylate were placed in 1.5 liters of acetonitrile. Thereto there was added a solution of 77 g (0.44 mol) of dipotassium hydrogen phosphate and 128 g (0.47 mol) of potassium peroxodisulphate in 660 ml of water and the mixture was heated to 100° C. The reaction time amounted to 2.5 hours. During this time the pH value of the mixture becomes acidic. This pH was held at about 5 by the portionwise addition of further dipotasium hydrogen phosphate. After completion of the reaction the acetonitrile was removed on a rotary evaporator and the aqueous residue was extracted with 3×250 ml of methylene chloride. The combined organic phases were washed once each time with 500 ml of 3% sodium hydrogen carbonate solution and 750 ml of saturated, aqueous sodium chloride solution and subsequently dried over magnesium sulphate. After concentration there was obtained a brown oil which was purified by chromatography [silica gel, 0.063–0.2 mm particle size, elution with 1) ethyl acetate:hexane=2:1; 2) ethyl acetate].

Yield: 37 g (45%)
IR (KBr): 1755,1689 cm$^{-1}$
MS (EI): (M—CONH) 203

In analogy to Example 1 there was made:

(b) t-Butoxy-(1S,5R)-7-oxo-6-sulpho-2,6-diazabicyclo[3.2.0]-heptane-2-carboxylate sodium salt IR (KBr): 1758, 1690
MS (M$^-$): 291

EXAMPLE 2

(1S,5R)-7-Oxo-2-(phenylcarbamoyl)-2,6-diazabicyclo-[3.2.0]heptane-6-sulphonic acid sodium salt was made in the same manner as given in Example 1.

IR (KBr): 1751, 1657 cm$^{-1}$
MS: (M–Na)$^-$310

The (1S,5R)-7-oxo-2-(phenylcarbamoyl)-2,6-diazabicyclo-[3.2.0]heptane used as the starting material for this was prepared as follows:

(1S,5R)-2,6-Diazabicyclo[3.2.0]heptan-7-one 34 g (0.14 mol) of benzyl (1S,5R)-6-(3,4-dimethoxybenzyl)-7-oxo-2,6-diazabicyclo[3.2.0]heptane-2-carboxylate were dissolved in 600 ml of ethanol, 34 g of 10% Pd/C and 130 ml of 1,4-cyclohexadiene were added thereto and this suspension was stirred under argon. An exothermic reaction begins after about 30 minutes, and it can be very vigorous. If necessary, the mixture should be cooled to 50° C. After about a further hour the reaction was finished completely, the suspension was filtered over a fluted filter and the filtrate was concentrated. The residue was recrystallized from ethanol.

Yield: 13.6 g (88%) of colourless crystals which rapidly become brown in air
M.p: 148°–150° C. (ethanol)
Elementary analysis: $C_5H_8N_2O$ Calc. C 53.56 H 7.19 N 24.98 Found C 53.27 H 7.28 N 24.67

(1S,5R)-7-Oxo-2-(phenylcarbamoyl)-2,6-diazabicyclo[3.2.0]heptane 100 mg (0.89 mmol) of (1S,5R)-2,6-diazabicyclo[3.2.0]heptan-7-one were dissolved in 5 ml of chloroform and heated to boiling under reflux. Phenyl isocyanate (0.1 ml, 0.89 mmol) and 1 drop of triethylamine were added. thereto and the mixture was left to react at the boiling temperature for 1 hour. After concentration the residue was chromatographed over silica gel (0.063–0.2 mm particle size) with ethyl acetate:ethanol=3:2.

Yield: 134 mg (65%)
$^1$H-NHR (250 MHz, CDCl$_3$): δ [ppm]=1.68–1.86 (4-H, m, 1H); 1.98 (4-H, dd, 1H, J=6 Hz, 14 Hz); 3.42 (3-H, m, 1H); 4.18 (3-H, dd, 1H, J=8 Hz); 4.30 (5-H, t, 1H, J=4 Hz); 5.37 (1-H, t, 1H J=4 Hz); 6.97 (arom., 1H); 7.23 (arom., 2H); 7.46 (arom., 2H); 7.76 (NH); 8.08 (NH)

EXAMPLE 3

(1S,5R)-2-(Benzylcarbamoyl)-7-oxo-2,6-diazabicyclo[3.2.0]heptane-6-sulphonic acid sodium salt was made in the same manner as given in Example 2

IR (KBr): 1746, 1636 cm$^{-1}$
Elementary analysis: $C_{13}H_{14}N_3O_5SNa$ Calc. C 44.96 H 4.06 N 12.10 S 9.23 Found C 45.45 H 4.12 N 12.27 S 9.07

The (1S,5R)-2-(benzylcarbamoyl)-7-oxo-2,6-diazabicyclo-[3.2.0]heptane used as the starting material for this was prepared analogously to Example 2:

$^1$H-NMR (250 MHz, CDCl$_3$): δ [ppm]=1.68–1.86 (4-H, m, 1H); 1.95 (4-H, dd, 1H, J=6 Hz, 14 Hz); 3.40 (3-H, m, 1H); 4.08 (3-H, dd br., 1H, J=8 Hz); 4.31 (5-H, t, 1H, J=4 Hz); 4.42 (PhCH$_2$, dd, 2H, J=6 Hz, 8 Hz); 4.97 (1-H, t, 1H, J=4 Hz); 5.24 (NH, t br.); 6.34 (NH, s br.); 7.3 (arom., 5H, m)

EXAMPLE 4

(a) Benzyl [(R)-α-[[(1S,5R)-7-oxo-6-sulpho-2,6-diazabicyclo-[3.2.0]hept-2-yl]carbonyl]benzyl] carbamate sodium salt 1.80 g (4.74 mmol) of benzyl [(R)-α-[[(1S,5R)-7-oxo-2,6-diazabicyclo[3.2.0]hept-2-yl]carbonyl]benzyl]carbamate were sulphonated according to Example 1.

Yield: 1.03 g (45%) of colourless powder
IR (KBr): 1760, 1717, 1652 cm$^{-1}$

Elementary analysis: $C_{21}H_{20}N_3O_7SNa$ Calc. C 52.39 H 4.19 N 8.73 Found C 52.53 H 4.16 N 8.74

(b) (1S,5R)-7-Oxo-2-(D-2-phenylglycyl)-6-2,6-diazabicyclo[3.2.0]heptane-6-sulphonic acid 400 mg (0.80 mmol) of benzyl [(R)-α-[[(1S,5R)-7-oxo-6-sulpho-2,6-diazabicyclo[3.2.0]hept-2-yl]carbonyl]benzyl]carbamate sodium salt were dissolved in 8 ml of water, treated with 0.47 ml of glacial acetic acid and hydrogenated at 25°–30° C. for 6.5 hours over 40 mg of 10% Pd/C. The mixture was filtered and fractionated over a polymeric hydrophobic gel with 1) water and 2) water:methanol 4:1. The fractions containing the product were combined and lyophilized.

Yield: 270 mg (80%) of colourless powder
IR (KBr): 1765, 1661 cm$^{-1}$

Elementary analysis: $C_{13}H_{15}N_3O_5S$ Calc. C 47.99 H 4.65 N 12.91 S 9.85 Found C 48.15 H 4.50 N 12.88 S 9.50

The benzyl [(R)-α-[[(1S,5R)-7-oxo-2,6-diazabicyclo[3.2.0]-hept-2-yl]carbonyl]benzyl]carbamate used above was prepared as follows:

(1S,5R)-6-(3,4-Dimethoxybenzyl)-7-oxo-2,6-diazabicyclo[3.2.0]-heptane

This compound was prepared analogously to Example 2 from benzyl (1S,5R)-6-(3,4-dimethoxybenzyl)-7-oxo-2,6-diazabicyclo[3.2.0]heptane-2-carboxylate by treatment with Pd/C and cyclohexadiene.

IR (film): 1731 cm$^{-1}$
MS (M–DMB)$^+$111

Benzyl [(R)-α-[[(1S,5R)-7-oxo-2,6-diazabicyclo[3.2.0]hept-2-yl]-carbonyl]benzyl]carbamate 2.00 g (7.62 mmol) of (1S,5R)-6-(3,4-dimethyoxybenzyl)-7-oxo-2,6-diazabicyclo[3.2.0]heptane and 2.1 ml (15.25 mmol) of triethylamine were dissolved in 45 ml of methylene chloride. While cooling with ice there were successively added thereto 2.61 g (9.15 mmol) of N-benzyloxycarbonyl-D-phenylglycine, 2.05 g (9.91 mmol) of DCC and 1.67 g (9.91 mmol) of HOBT, the mixture was stirred for 1 hour while cooling with ice and overnight at room temperature. For the work-up, the resulting suspension was again brought into solution with 100 ml of methylene chloride, subsequently extracted in each case once with 60 ml of 2% citric acid solution, 50 ml of saturated, aqueous sodium hydrogen carbonate solution, 100 ml of water and 100 ml of saturated aqueous sodium chloride solution. It was dried over magnesium sulphate and concentrated. The oily residue was chromatographed on 120 g of silica gel (particle size 0.063–0.2mm) with ethyl acetate. 3.24 g (80%) of benzyl [(R)-a-[[(1S,5R)-6-(3,4-dimethoxybenzyl)-7-oxo-2,6-diazabicyclo[3.2.0]hept-2-yl]carbonyl]benzyl]carbamate were obtained therefrom. The dimethoxybenzyl protecting group was removed analogously to Example 1 by treatment with potassium peroxodisulphate and 1.80 g (87.6%) of the product were obtained.

IR (Kbr): 1768, 1717, 1648 cm$^{-1}$
MS: (M+Na)$^+$402

In analogy thereto there was made:

(c) Benzyl [(S)-α-[[(1S,5R)-7-oxo-6-sulpho-2,6-diazabicyclo-[3.2.0]hept-2-yl]carbonyl]benzyl]carbamate sodium salt IR (KBr): 1760, 1716 cm$^{-1}$ Elementary analysis: $C_{21}H_{20}N_3O_7SNa$ Calc. C 52.39 H 4.19 N 8.73 S 6.66 Found C 52.79 H 4.28 N 8.76 S 6.42

(d) (1S,5R)-7-Oxo-2-(L-2-phenylglycyl)-2,6-diazabicyclo-[3.2.0]heptane-6-sulphonic acid IR (KBr): 1766, 1660 cm$^{-1}$
MS: (M–Na)$^-$324

(e) (1S,5R)-2-[N-[(Benzyloxy)carbonyl]-3-phenyl-D-alanyl]-7-oxo-6-2,6-diazabicyclo[3.2.0]heptane-6-sulphonic acid sodium salt IR (KBr): 1759, 1717, 1650 cm$^{-1}$ Elementary analysis: $C_{22}H_{22}N_3O_7SNa$ Calc. C 53.33 H 4.48 N 8.48 S 6.47 Found C 53.82 H 4.54 N 8.59 S 6.09

(f) (1S,5R)-7-Oxo-2-(3-phenyl-D-alanyl)-2,6-diazabicyclo-[3.2.0]heptane-6-sulphonic acid IR (KBr): 1765, 1658 cm$^{-1}$
MS: (M+H)$^+$340

(g) Benzyl [[[(1S,5R)-7-oxo-6-sulpho-2,6-diazabicyclo[3.2.0]-hept-2-yl]carbonyl]methyl]carbamate IR (KBr): 1758, 1717, 1653 cm$^{-1}$
MS: (M–Na)$^-$382

EXAMPLE 5

(a) (1S,5R)-2-[(E)-3-(2-Furyl)acryloyl]-7-oxo-2,6-diaza-bicyclo[3.20]heptane-6-sulphonic acid sodium salt was made by sulphonation in the same manner as given in Example 1

IR (KBr): 1753, 1650, 1605 cm$^{-1}$

Elementary analysis: $C_{12}H_{11}N_2O_6Na$ Calc. C 43.12 H 3.22 N 8.38 S 9.59 Found C 43.39 H 3.13 N 8.46 S 9.44

The (1S,5R)-2-[(E)-3-(2-furyl)acryloyl]-2,6-diazabicyclo-[3.2.0]heptan-7-one used for this was prepared as follows:

500 mg (4.46 mmol) of (1S,5R)-2,6-diazabicyclo-[3.2.0]heptan-7-one and 1.4 ml (9.82 mmol) of triethylamine were dissolved in 50 ml of dichloromethane and cooled with ice under argon. Thereto there were added in succession 678 mg (4.91 mmol) of 3-(2-furyl)acrylic acid, 1.20 g (5.80 mmol) of DCC and 980 mg (5.80 mmol) of HOBT. The mixture was left to react for 1 hour while cooling with ice and overnight at room temperature. Thereafter, the mixture was extracted in each case once with 2% citric acid solution, saturated sodium hydrogen carbonate solution, water and saturated sodium chloride solution. The organic phase was dried over magnesium sulphate and concentrated. The oily residue was chromatographed over silica gel (Merck, 0.063–0.2 mm particle size) with ethyl acetate:ethanol=3:2.

Yield: 450 mg (43%)

$^1$H-NMR (250 MHz, CDCl$_3$): (rotamers in the ratio 2:1) δ [ppm]=1.02–1.46 (4-H,m,br.,1H); 2.05 (4-H,m,br.,1H); 3.49 and 3.68 (3-H,m,br.,1H); 4.13–4.52 (3-H,7-H,m br., 2H); 5.24 and 6.71 (1-H,s br.,1H); 6.46 (furan-β-H,m,2H); 6.59 (furan-α-H,d,1H,J=Hz); 6.75 (=CH,d,1H,J=16 Hz); 7.46 (NH,s,1H); 7.50 (=CH,d,1H,J=16 Hz).

In analogy to Example 5(a) there were made:

(b) (1S,5R)-7-Oxo-2-(N-phenylglycyl)-2,6-diazabicyclo-[3.2.0]heptane-6-sulphonic acid sodium salt IR (KBr): 1756, 1650 cm$^{-1}$ Elementary analysis: $C_{13}H_{14}N_3O_5SNa$ Calc. C 44.96 H 4.06 N 12.10 S 9.23 Found C 45.20 H 3.99 N 12.15 S 9.01

(c) Benzyl [(RS)-α-[[(1S,5R)-7-oxo-6-sulpho-2,6-diazabicyclo-[3.2.0]hept-2-yl]-carbonyl]-2-thienyl]carbamate sodium salt IR (KBr): 1760, 1716, 1655 cm$^{-1}$ Elementary analysis: $C_{19}H_{18}N_3O_7S_2Na$ Calc. C 44.81 H 3.72 N 8.62 S 13.15 Found C 46.73 H 3.62 N 8.63 S 13.00

(d) t-Butyl [(R or S)-α-[[(1S,5R)-7-oxo-6-sulpho-2,6-diazabicyclo[3.2.0]hept-2-yl]-carbonyl]-2-thienyl]carbamate sodium salt IR (KBr): 1762, 1709, 1656 cm$^{-1}$ Elementary analysis: $C_{16}H_{20}N_3O_7S_2Na$ Calc. C 42.38 H 4.45 N 9.27 S 14.14 Found C 42.17 H 4.60 N 9.29 S 13.95

(e) (1S,5R)-2-[(R or S)-α-Amino-(2-thienyl)acetyl]-7-oxo-2,6-diazabicyclo[3.2.0]heptane-6-sulphonic acid IR (KBr): 1767, 1664 cm$^{-1}$ Elementary analysis: $C_{11}H_{13}N_3O_5S_2$ Calc. C 44.96 H 4.06 N 12.10 S 9.23 Found C 45.20 H 3.99 N 12.15 S 9.01

(f) (1S,5R)-2-[(Z)-3-α-Acetamidocinnamoyl]-7-oxo-2,6-diazabicyclo[3.2.0]heptane-6-sulphonic acid sodium salt IR (KBr): 1759, 1628 cm$^{-1}$ Elementary analysis: $C_{16}H_{16}N_3O_6SNa$ Calc. C 47.88 H 4.02 N 10.47 S 7.99 Found C 47.01 H 4.13 N 10.42 S 7.73

(g) (1S,5R)-2-[D- or L-N-Acetyl-2-phenylglycyl]-7-oxo-2,6-diazabicyclo[3.2.0]-heptane-6-sulphonic acid sodium salt IR (KBr): 1761, 1648 cm$^{-1}$ Elementary analysis: $C_{15}H_{16}N_3O_6SNa$ Calc. C 46.27 H 4.14 N 10.79 S 8.23 Found C 45.50 H 4.00 N 10.55 S 8.03

(h) (1S,5R)-2-[(R,S)-2-Benzamido-4-(methylthio)butyryl]-7-oxo-2,6-diazabicyclo[3.2.0]heptane-6-sulphonic acid sodium salt IR (KBr): 1760, 1641 cm$^{-1}$ Elementary analysis: $C_{17}H_{20}N_3O_6S_2Na$ Calc. C 45.43 H 4.49 N 9.35 S 14.27 Found C 45.66 H 4.82 N 9.37 S 14.13

(i) (1S,5R)-2-[N-(m-Aminophenyl)glycyl]-7-oxo-2,6-diazabicyclo[3.2.0]heptane-6-sulphonic acid $^1$H-NMR (250 MHz, DMSO-d$_6$): (rotamers in the ratio of 3:2) δ [ppm]: 1.72 (4-H,m,1H); 2.34 (4-H,m,1H); 3.14 (3-H,m, 1H); 3.86 (3-H,m,1H); 4.02 (Ar—CH$_2$,m,2H); 4.34 and 4.52 (5-H,t,1H,J=4 Hz); 5.22 and 5.26 (1-H,d,1H,J=4 Hz); 6.00 (3 arom. H); 6.62 (1 arom. H).

(j) (1S,5R)-2-[[(1-Methyl-1H-tetrazol-5-yl)-thio]acetyl]-7-oxo-2,6-diazabicyclo[3.2.0]heptane-6-sulphonic acid sodium salt IR (KBr): 1758, 1646 cm$^{-1}$ MS (M–Na)$^-$: 347

(k) (1S,5R)-2-[[1H-Benzotriazol-1-yl)oxy]acetyl]-7-oxo-2,6-diazabicyclo[3.2.0]-heptane-6-sulphonic acid sodium salt IR (KBr): 1760, 1663 cm$^{-1}$ Elementary analysis: $C_{13}H_{12}N_5O_6SNa$ Calc. C 40.11 H 3.11 N 17.99 Found C 40.29 H 3.12 N 17.62

(l) (1S,5R)-2-[(2-Isopropyl-2H-tetrazol-5-yl)-acetyl]-7-oxo-2,6-diazabicyclo[3.2.0]heptane-6-sulphonic acid sodium salt IR(KBr): 1760, 1652 cm$^{-1}$ MS (ISN): 342.8 (M–Na)$^-$ (m) (1S,5R)-2-[[(5-Methyl-1,3,4-thiadiazol-2-yl)thio]acetyl]-7-oxo-2,6-diazabicyclo[3.2.0]heptane-6-sulphonic acid sodium salt IR (KBr): 1757, 1642 cm$^{-1}$ Elementary analysis: $C_{10}H_{11}N_4O_5S_3Na$ Calc. C 31.09 H 2.87 N 14.50 Found. C 30.93 H 3.11 N 14.62

(n) (1S,5R)-2-[N-[2-Oxo-4-(trifluoromethyl)-2H-1-benzopyran-7-yl]glycyl]-7-oxo-2,6-diazabicyclo[3.2.0]heptane-6-sulphonic acid sodium salt IR (KBr): 1748, 1642 cm$^{-1}$ Elementary analysis: $C_{17}H_{13}F_3N_3O_7SNa$ Calc. C 42.24 H 2.71 N 8.69 S 6.63 Found. C 42.61 H 2.66 N 8.74 S 6.75

(o) [(1S,5R)-2-[[N-[(Benzyloxy)carbonyl]propionyl]-7-oxo-6-sulpho-2,6-diazabicyclo[3.2.0]heptan-2-yl]ethyl]carbamate sodium salt IR (KBr): 1758, 1712, 1637 cm$^{-1}$

MS (M+H)$^+$: 420.

(p) (1S,5R)-2-[(6-Hydroxy-pyridazin-3-yloxy)-acetyl]-7-oxo-2,6-diazabicyclo[3.2.0]heptane-6-sulfonic acid sodium salt IR(KBr): 1761, 1654 cm$^{-1}$ MS(ISN): 343.0 (M–Na)$^+$ (q) (1S,5R)-7-Oxo-2-[(1-phenyl-tetrazol)-5-ylsulfanyl-acetyl]-2,6-diazabicyclo[3.2.0]heptane-6-sulfonic acid sodium salt IR(KBr): 1758, 1651 cm$^{-1}$ Elementary analysis: $C_{14}H_{13}N_6O_5S_2Na$ calcd. C38.89 H3.03 N19.4 S14.83 found C39.23 H3.12 N19.60 S14.76

EXAMPLE 6

(a) t-Butyl [(S)-p-hydroxy-α-[[(1S,5R)-7-oxo-6-sulpho-2,6-diazabicyclo[3.2.0]hept-2-yl]carbonyl]phenyethyl]carbamate triethylamine salt A solution of (1S,5R)-7-oxo-2,6-diazabicyclo[3.2.0]heptane-6-sulphonic acid trifluoroacetate (360 mg, 1.17 mmol) dissolved in abs. DMF (30 ml) was treated with t-butylcarbonyl-L-tyrosine hydroxysuccinimide (440mg, 1.16 mmol) and triethylamine (120 mg, 1.2 mmol). After stirring for 4 days the DMF was evaporated. The residue was chromatographed over a polymeric, hydrophobic gel (eluent water, then water:methanol 4:1). The fractions containing the product were combined and lyophilized.

Yield: 250 mg (38%)

IR (KBr): 1771, 1709, 1650 cm$^{-1}$

Elementary analysis: $C_{25}H_{40}N_4O_8S$ Calc. C 53.94 H 7.24 N 10.06 Found C 54.05 H 7.18 N 10.16

(b) (1S,5R)-7-Oxo-2-L-tyrosyl-2,6-diazabicyclo[3.2.0]heptane-6-sulphonic acid t-Butyl [(S)-p-hydroxy-α-[[(1S,5R)-7-oxo-6-sulpho-2,6-diazabicyclo[3.2.0]hept-2-yl]carbonyl]phenethyl]carbamate triethylamine salt (180 mg, 0.32 mmol), pre-cooled to −10° C., was treated with trifluoroacetic acid (4 ml). The excess trifluoroacetic acid was removed under reduced pressure after 45 minutes. The residue was chromatographed over a polymeric, hydrophobic gel (75–150 g) (eluent water, then water:methanol 10:1). The fractions containing the product were combined and lyophilized.

Yield: 80 mg (70%)

IR (KBr): 1756, 1657, 1613 cm$^{-1}$

Elementary analysis: $C_{14}H_{17}N_3O_6S$ Calc. C 47.32 H 4.82 N 11.82 Found C 46.58 H 4.94 N 11.52

The (1S,5R)-7-oxo-2,6-diazabicyclo[3.2.0]heptane-6-sulphonic acid trifluoroacetate used as the starting material was prepared as follows:

t-Butoxy (1S,5R)-7-oxo-6-sulpho-2,6-diazabicyclo[3.2.0]heptane-2-carboxylate sodium salt (1,1 g 3.5 mmol), pre-cooled to −10° C., was treated with trifluoroacetic acid (10 ml). After one hour the reaction mixture was diluted with ether. The crystals obtained were filtered off under suction and washed with ether.

Yield: 1 g (93%).

IR (KBr): 1752 cm$^{-1}$

MS: (M+Na) 237

In analogy to Example 6 there were made:

(c) t-Butyl [(R)-p-hydroxy-et-[[(1S,5R)-7-oxo-6-sulpho-2,6-diazabicyclo[3.2.0]hept-2-yl]carbonyl]benzyl]carbamate triethylamine salt (1:1)

IR (KBr): 1770, 1708, 1651 cm$^{-1}$

MS: (M−TEA) 439

(d) (1S,5R)-2-[D-2-(p-Hydroxyphenyl)glycyl]-7-oxo-2,6-diazabicyclo[3.2.0]-heptane-6-sulphonic acid IR (KBr): 3418, 1766, 1660 cm$^{-1}$

MS: (M−H) 340

(e) (R/S)-α-(1S,5R)-2-[2-carboxy-2-(3-thienyl)acetyl]-7-oxo-2,6-diazabicyclo[3.2.0]heptane-6-sulphonic acid triethylamine salt (1:1)

IR (KBr): 3437, 1768, 1647 cm$^{-1}$ (f) (1S,5R)-2-[(E)-3-(3-Indolyl)acryloyl]-7-oxo-2,6-diazabicyclo[3.2.0]heptane-6-sulphonic acid triethylamine salt (1:1)

IR: 3418, 1764, 1640 cm$^{-1}$

MS: (M−TEA) 360

(g) t-Butyl [(S)-2-indol-3-yl-1-[[(1S,5R)-7-oxo-6-sulpho-2,6-diazabicyclo[3.2.0]hept-2-yl]carbonyl]ethyl]carbamate triethylamine salt (1:1)

IR (KBr): 1767, 1707, 1648 cm$^{-1}$

MS: (M−TEA) 681; (M+H) 580

Elementary analysis: $C_{27}H_{41}N_5O_7S$ Calc. C 55.94 H 7.13 N 12.08 Found C 55.59 H 7.08 N 12.11

(h) (1S,5R)-7-Oxo-2-L-tryptophanyl-2,6-diazabicyclo[3.2.0]heptane-6-sulphonic acid IR (KBr): 1764, 1657 cm$^{-1}$

MS: (M+H) 379

(i) (1S,5R)-7-Oxo-2-(3-pyridylacetyl)-2,6-diazabicyclo[3.2.0]-heptane-6-sulphonic acid sodium salt IR: 1760,1649, 1555 cm$^{-1}$ MS: (M−Na) 309

(j) (1S,5R)-2-[(RS)-2-Indolylcarbonyl-7-oxo-2,6-diazabicyclo-[3.2.0]heptane-6-sulphonic acid triethylamine salt (1:1)

IR (KBr): 1765, 1652 cm$^{-1}$

MS: M(−TEA) 336

Elementary analysis: $C_{20}H_{30}N_4O_5S$ Calc. C 54.78 H 6.90 N 12.78 Found C 54.76 H 7.12 N 13.09

(k) (1S,5R)-2-[(R)-α-Hydroxyphenylacetyl]-7-oxo-2,6-diazabicyclo[3.4.0]heptane-6-sulphonic acid sodium salt (1:1)

IR (KBr): 1759, 1649 cm$^{-1}$

MS: (M+H) 349

(l) (1S,5R)-2-[(S)-α-Hydroxyphenylacetyl]-7-oxo-2,6-diazabicyclo[3.2.0]heptane-6-sulphonic triethylamine salt (1:1)

IR (KBr): 1765, 1646 cm$^{-1}$

MS: (M+H) 428; (M+TEA) 529

(m) 5-Benzyl 1-t-butyl [(S)-1-[[(1S,5R)-7-oxo-6-sulpho-2,6-diazabicyclo[3.2.0]hept-2-yl]carbonyl]pentamethylene]-dicarbamate triethylamine salt (1:1)

IR: 1768, 1711, 1650 cm$^{-1}$

MS: (M−TEAH$^+$) 553

Elementary analysis: $C_{30}H_{49}N_5O_9S$ Calc. C 54.94 H 7.73 N 10.68 Found C 54.25 H 7.36 N 10.57

(n) (1S,5R)-2-[N6-[(Benzyloxy)carbonyl]-L-lysyl]-7-oxo-2,6-diazabicyclo[3.2.0]-heptane-6-sulphonic acid IR (KBr): 1768, 1695, 1665 cm$^{-1}$

MS: 453

Elementary analysis: $C_{19}H_{26}N_4O_7S$ Calc. C 50.21 H 5.77 N 12.33 Found C 50.08 H 5.74 N 12.22

(o) (1S,5R)-2-[(2-Amino-4-thiazolyl)acetyl]-7-oxo-2,6-diazabicyclo[3.2.0]heptane-6-sulphonic acid triethylamine salt IR (KBr): 1767, 1635 cm$^{-1}$

MS=434 (M+H)

(p) (1S,5R)-2-[R-2-(m-Hydroxyphenyl)glycyl]-7-oxo-2,6-diazabicyclo[3.2.0]heptane-6-sulphonic acid IR (KBr): 1767, 1661 cm$^{-1}$ Elementary analysis: $C_{13}H_{15}N_3O_6S$ Calc. C 45.74 H 4.43 N 12.31 Found C 45.82 H 4.09 N 12.22

(q) (1S,5R)-2-[DL -2-(m-Hydroxyphenyl)glycyl]-7-oxo-2,6-diazabicyclo[3.2.0]heptane-6-sulphonic acid IR (KBr): 1765, 1658 cm$^{-1}$ Elementary analysis: $C_{13}H_{15}N_3O_6S$ Calc. C 45.74 H 4.43 N 12.3 1 Found C 45.30 H 4.29 N 11.85

(r) (1S,5R)-2-[DL-2-(2-Amino-4-thiazolyl)glycyl]-7-oxo-2,6-diazabicyclo[3.2.0]heptane-6-sulphonic acid triethylamine salt IR (KBr): 1767, 1670 cm$^{-1}$

MS=348 (M+H)

(s) (1S,5R)-2-[R,S-Amino-(4-hydroxyphenyl)-
acetyl]-7-oxo-2,6-diazabicyclo[3.2.0]heptane-6-
sulphonic acid sodium salt IR (KBr): 1766, 1659 cm$^{-1}$
MS=340 (M–H)

(t) (1S,5R)-(E)-2-[3-(4-Hydroxy-phenyl)acryloyl]-7-
oxo-2,6-diazabicyclo[3.2.0]heptane-6-sulphonic acid
sodium salt IR (KBr): 1753, 1644 cm$^{-1}$
MS=336 (M–Na).

(u) (1S,5R)-(E)-2-[3-(3,4Dihydroxy)phenyl)
acryloyl)]-7-oxo-2,6-diazabicyclo[3.2.0]heptane-6-
sulfonic acid sodium salt IR(KBr): 1757, 1644 cm$^{-1}$
MS (ISN): 353.2 (M–H)$^-$ (v) (1S,5R)-2-(4-Hydroxy-phenylaminoacetyl)-7-
oxo-2,6-diazabicyclo[3.2.0]heptane-6-sulfonic acid
sodium salt IR(KBr): 1759, 1648, 1517 cm$^{-1}$
MS (ISN): 340.1 (M–Na)$^-$ (w) (1S,5R)-2-[5-(5-Amino -1,3,4-thiadiazol-2-
ylsulfanylacetylamino)-1,3,4-thiadiazol-2-
ylsulfanylacetyl]-7-oxo-2,6-diazabicyclo[3.2.0]
heptane-6-sulfonic acid sodium salt IR(KBr): 1760, 1635 cm$^{-1}$
MS (ISN): 537.1 (M–Na)$^-$

EXAMPLE 7

(1as,3aR,6bR)-1,1a,3a,6b-Tetrahydro-5-methoxy-1-
oxo-2,6a-diazacyclobuta[cd]indene-2,6(3H,4H)-
dicarboxylic acid 2-t-butyl monoester A solution of 2-t-butyl 6-(p-nitrobenzyl) (1as,3aR,6bR)-
1,1 a,3 a,6b-tetrahydro-5-methoxy-1-oxo-2,6-
diazabicyclobuta[cd]indene-2,6(3H,4H)-dicarboxylate (200
mg, 0.43 mmol) in ethyl acetate (20 ml) was hydrogenated
over 10% Pd/C. The catalyst was filtered off and the solution
was evaporated. The residue was taken up in CH$_2$Cl$_2$ and
treated with a NaHCO$_3$ solution (160 mg in 10 ml of water).
The aqueous phase was extracted with CH$_2$Cl$_2$ (2×50 ml)
and finally adjusted to pH 4 with 1N HCl (2 ml). The
aqueous phase was extracted with CH$_2$Cl$_2$ (3×100 ml). After
drying, evaporation and crystallization (ethyl acetate/n-
hexane) there were obtained 70 mg (49%) of (1as,3aR,6bR)
-1,1a3a,6b-tetrahydro-5-methoxy-1-oxo-2,6-
diazabicyclobuta[cd]indene-2,6(3H,4H)-dicarboxylic acid
2-t-butyl monoester.

IR (KBr): 1761, 1669 cm$^{-1}$

Elementary analysis: C$_{15}$H$_{20}$N$_2$O$_6$ Calc. C 55.55 H 6.22
N 8.64 Found C 55.12 H 6.25 N 8.57

The 2-t-butyl 6-(p-nitrobenzyl) (1as,3aR,6bR)-1,1a3a,6b-
tetrahydro-5-methoxy-1-oxo-2,6a-diazabicyclobuta[cd]
indene-2,6(3H,4H)-dicarboxylate used as the starting mate-
rial was prepared as follows:

Benzyl (1S,5S)-6-(3,4-dimethoxybenzyl)-4,7-dioxo-
2,6-diazabicyclo[3.2.0]heptane-2-carboxylate 3.7 g (47 mmol) of DMSO were dissolved in 50 ml of
methylene chloride and cooled to –78° C. under argon.

Then, 5 ml (35 mmol) of trifluoroacetic acid anhydride were
added dropwise thereto, the mixture was stirred for 15
minutes and a solution of 9.7 g (23.5 mmol) of benzyl
(1S,4S,5S)-6-(3,4-dimethoxybenzyl)-4-hydroxy-7-oxo-2,6-
diazabicyclo[3.2.0]heptane-2-carboxylate in 50 ml of meth-
ylene chloride was slowly added dropwise thereto and left to
react for 1.5 hours. Before it was left to warm to room
temperature, 12 ml (70 mmol) of ethyldiisopropylamine
were added thereto. The reaction mixture was then washed
once each time with dilute aqueous hydrochloric acid,
saturated aqueous sodium hydrogen carbonate solution and
saturated aqueous sodium chloride solution and the organic
phase was dried over magnesium sulphate. After concentra-
tion there were obtained 9.5 g (98%) of a yellow oil.

IR (film): 1760, 1709 cm$^{-1}$
MS: (M+) 410

In the same manner there was prepared:

t-Butyl-(1S,5S)-6-(2,4-dimethoxybenzyl)-4,7-dioxo-
2,6-diazabicyclo[3.2.0]heptane-2-carboxylate Yield: 90%

NMR (250 MHz, δ ppm, CDCl$_3$): 1.49 (s,9H), 3.80 and
3.82 (2s,2x3H), 3.86 (d,J=4 Hz,1 Hz), 4.05 (broad s,2H),
4.10 (d,J=16 Hz,1H), 4.54 (d,J=16 Hz,1 Hz), 5.11 and 5.40
(broad s1H), 6.44 (m,2H), 7.13 (m,1H).

t-Butyl (1S,5R)-6-(2,4-dimethoxybenzyl)-4-[(2,2-
dimethyl-4-oxo-4H-m-dioxan-6-yl)methylene]-7-
oxo-2,6-diazabicyclo[3.2.0]heptane-2-carboxylate A solution of t-butyl (1S,5S)-6-(2,4-dimethoxybenzyl)-4,
7-dioxo-2,6-diazabicyclo[3.2.0]heptane-2-carboxylate (1.61
g, 4.28 mmol) in acetonitrile (50 ml) was treated with
2,2-dimethyl-6-[(triphenylphosphoranylidene)methyl]-4H-
1,3-dioxan-4-one (2.06 g, 5.13 mmol) and stirred for 48
hours. The solvent was evaporated and the residue was
chromatographed over silica gel (eluent CH$_2$Cl$_2$:ethyl
acetate 65:35) and crystallized from ethyl acetate. There
were obtained 2.07 g (97%) of t-butyl (1S,5R)-6-(2,4-
dimethoxybenzyl)-4-[(2,2-dimethyl-4-oxo-4H-m-dioxan-6-
yl)methylene]-7-oxo-2,6-diazabicyclo[3.2.0]heptane-2-
carboxylate. M.p. 171°–172° C.

IR (KBr): 1747, 1721, 1696 cm$^{-1}$

Elementary analysis: C$_{26}$H$_{32}$N$_2$O$_8$ Calc. C 62.39 H 6.44
N 5.60 Found C 61.85 H 6.63 N 5.21 t-Butyl (1S,4R,5R)-6-(2,4-dimethoxybenzyl)-4-[(2,
2-dimethyl-4-oxo-4H-m-dioxan-6-yl)methyl]-7-oxo-
2,6-diazabicyclo[3.2.0]heptane-2-carboxylate A solution of t-butyl (1S,5R)-6-(2,4-dimethoxybenzyl)-4-
[(2,2-dimethyl-4-oxo-4H-m-dioxan-6-yl)methylene]-7-oxo-
2,6-diazabicyclo[3.2.0]heptane-2-carboxylate (9.85 g, 19.68
mmol) was dissolved in THF:ethyl acetate 1:1 (300 ml) and
hydrogenated over Pd/C. After filtering off the catalyst and
evaporation of the solvent the residue was crystallized from
ethyl acetate. There were obtained 7.67 g (77.5%) of t-butyl
(1S,4R,5R)-6-(2,4-dimethoxybenzyl)-4-[(2,2-dimethyl-4-
oxo-4H-m-dioxan -6-yl)methyl]-7-oxo-2,6-diazabicycio
[3.2.0]heptane-2-carboxylate. M.p. 152°–154° C.

IR (KBr): 1748, 1725, 1690 cm$^{-1}$

Elementary analysis: C$_{26}$H$_{34}$N$_2$O$_8$ Calc. C 62.14 H 6.82
N 5.57 Found C 62.18H 6.98 N 5.58 t-Butyl (1S,4R,5R)-4-[(2,2-dimethyl-4-oxo-4H-m-
dioxan-6-yl)methyl]-7-oxo-2,6-diazabicyclo[3.2.0]
heptane-2-carboxylate was obtained in, 69% yield
in analogy to Example 1 by treating t-butyl (1S,4R,
5R)-6-(2,4-dimethoxybenzyl)-4-[(2,2-dimethyl-4-
oxo-4H-m-dioxan-6-yl)methyl]-7-oxo-2,6-
diazabicyclo[3.2.0]heptane-2-carboxylate with
potassium peroxodisulphate IR (KBr): 1774, 1731, 1701 cm$^{-1}$ Elementary analysis: $C_{17}H_{24}N_2O_6$ Calc. C 57.94 H 6.87 N 7.95 Found C 57.63 H 6.68 N 7.64 p-Nitrobenzyl (1S,4R,5R)-2-(t-butoxycarbonyl)-β,7-dioxo-2,6-diazabicyclo[3.2.0]heptane-4-butyrate A solution of t-butyl (1S,4R,5R)-4-[(2,2-dimethyl-4-oxo-4H-m-dioxan-6-yl)methyl]-7-oxo-2,6-diazabicyclo[3.2.0]heptane-2-carboxylate (3.5 g, 9.93 mmol) was dissolved in toluene (25 ml), treated with p-nitrobenzyl alcohol (1.52 g, 9.93 mmol) and heated to 110° C. for one hour. After evaporation of the solvent the residue was chromatographed on silica gel (eluent ethyl acetate:n-hexane 8:2) and recrystallized from ethyl acetate:n-hexane. There were obtained 3.31 g (74%) of p-nitobenzyl (1S,4R,5R)-2-(t-butoxycarbonyl)-β,7-dioxo-2,6-diazabicyclo[3.2.0]heptane-4-butyrate. M.p. 107°–110° C.

IR (KBr): 1770, 1749, 1694 cm$^{-1}$

Elementary analysis: $C_{21}H_{25}N_3O_8$ Calc. C 56.37 H 5.63 N 9.39 Found C 56.89 H 5.83 N 9.21 t-Butyl (1S,4R,5R)-4-[3-diazo-3[[(p-nitrobenzyl)oxy]carbonyl]-acetonyl]-7-oxo-2,6-diazabicyclo[3.2.0]heptane-2-carboxylate A solution of p-nitrobenzyl (1S,4R,5R)-2-(t-butoxycarbonyl)-β,7-dioxo-2,6-diazabicyclo[3.2.0]heptane-4-butrate (2.28 g, 5.1 mmol) was dissolved in acetonitrile (100 ml) and treated at about 0° C. with triethylamine (0.85 ml, 6.11 mmol) and tosyl azide (1.10 g, 5.61 mmol). The solvent was evaporated after one hour. The residue was taken up in methylene chloride and washed with 10% aqueous sodium chloride solution. After drying and evaporation of the solvent the residue was chromatographed on silica gel (eluent ethyl acetate:n-hexane 6:4) and recrystallized (ethyl acetate/n-hexane). There were obtained 2.08 g (86%) of t-butyl (1S,4R,5R)-4-[3-diazo-3-[[(p-nitrobenzyl)oxy]carbonyl]acetonyl]-7-oxo-2,6-diazabicyclo[3.2.0]-heptane-2-carboxylate, m.p. 132°–134° C.

IR (KBr): 2135, 1762, 1710, 1655 cm$^{-1}$

Elementary analysis: $C_{21}H_{23}N_5O_8$ Calc. C 53.38 H 4.90 N 14.79 Found C 53.29 H 4.89 N 14.78

2-t-Butyl 6-(p-nitrobenzyl) (1as,3aR,6bR)-1,1a3a,6b-tetrahydro-5-hydroxy-1-oxo-2,6a-diazabicyclo[cd]indene-2,6(3H,4H)-dicarboxylate A solution of 447 mg (0.9 mmol) of t-butyl (1S,4R,5R)-4-[3-diazo-3-[[(p-nitrobenzyl)oxy]carbonyl]acetonyl]-7-oxo-2,6-diazabicyclo[3.2.0]heptane-2-carboxylate in methylene chloride (20 ml) was treated with rhodium(II) caprylate (20 mg). The solvent was evaporated after one hour and the residue was chromatographed on silica gel (eluent ethyl acetate/n-hexane 6:4) and recrystallized (ether). There were obtained 180 mg (43%) of 2-t-butyl 6-(p-nitrobenzyl) (1as,3aR,6bR)-1,1 a,3a,6b-tetrahydro-5-hydroxy-1-oxo-2,6a-diazabicyclo[cd]indene-2,6(3H,4H)-dicarboxylate. M.p. 162°–164° C.

Ir (KBr): 1769, 1710 cm$^{-1}$

Elementary analysis: $C_{21}H_{23}N_3O_8$ Calc. C 56.63 H 5.20 N 9.43 Found C 56.54 H 5.49 N 9.29

2-t-Butyl 6-(p-nitrobenzyl) (1as,3aR,6bR)-1,1a3a,6b-tetrahydro-5-methoxy-1-oxo-2,6a-diazabicyclo[cd]indene-2,6(3H,4H)-dicarboxylate A solution of 2-t-butyl 6-(p-nitrobenzyl) (1as,3aR,6bR)-1,1 a,3a,6b-tetrahydro-5-hydroxy-1-oxo-2,6a-diazabicyclo[cd]indene-2,6(3H,4H)-dicarboxylate (359 mg, 0.91 mmol) in THF (2 ml) was treated with an ethereal diazomethane solution (3 ml, 1%) and stirred overnight. After evaporation of the solvent the residue was chromatographed over silica gel (eluent ethyl acetate:n-hexane 8:2) and recrystallized (ethyl acetate/n-hexane). There were obtained 222 mg (60%) of 2-t-butyl 6-(p-nitrobenzyl) (1as,3aR,6bR)-1,1a3a,6b-tetrahydro-5-methoxy-1-oxo-2,6a-diazabicyclo[cd]indene-2,6(3H,4H)dicarboxylate. M.p. 160°–161° C.

IR: 1760, 1713, 1690 cm$^{-1}$

Elementary analysis: $C_{22}H_{25}N_3O_8$ Calc. C 57.51 H 5.48 N 9.15 Found C 57.43 H 5.48 N 9.01

EXAMPLE 8

(a) (1S,5R)-2-[(E)-3-(2-Thienyl)acryloyl]-7-oxo-2,6-diazabicyclo[3.2.0]heptane-6-sulphonic acid was made by sulphonation in the same manner as given in Example 1

IR (KBr): 1751, 1639 cm$^{-1}$

MS (M–Na): 327

The (1S,5R)-2-[(E)-3-(2-thienyl)acryloyl]-2,6-diazabicyclo[3.2.0]heptane-7-one used for this was prepared as follows:

The solution of 510 mg (2.14 mmol) of pivaloyl-3-(2-thienyl)acryloyl anhydride in 2 ml of methylene chloride was added dropwise while cooling with ice to 200 mg (1.78 mmol) of triethylamine in 8 ml of methylene chloride. The mixture was left to stir at this temperature for 2 hours, thereafter concentrated and the oily residue was taken up in ethyl acetate. The solution was washed in succession with water, 2% aqueous citric acid solution, saturated aqueous sodium hydrogen carbonate solution and saturated aqueous sodium chloride solution, dried over magnesium sulphate and concentrated. There was obtained a yellow oil which crystallized.

Yield 150 g (34%)

IR (KBr): 1751, 1715, 1645 cm$^{-1}$

MS (M–CONH): 205

In the same manner there were made:

(b) (1S,5R)-7-Oxo-2-(1H-tetrazol-1-ylacetyl)-2,6-diazabicyclo[3.2.0]heptane-6-sulphonic acid sodium salt IR (KBr): 1762, 1665 cm$^{-1}$ MS (EI): 301,1 (M–Na)$^-$ (c) (1S,5R)-2-[DL-2-(o-Fluorophenyl)glycyl]-7-oxo-2,6-diazabicyclo[3.2.0]heptane-6-sulphonic acid sodium salt IR (KBr): 1768, 1667 cm$^{-1}$ Elementary analysis: $C_{13}H_{14}FN_3O_5S$ Calc. C 45.48 H 4.11 N 12.24 S 9.34 Found C 45.74 H 4.16 N 12.16 S 9.16

(d) (1S,5R)-2-[(E)-3-(4-Imidazolyl)acryloyl]-7-oxo-2,6-diazabicyclo[3.2.0]heptane-6-sulphonic acid sodium salt IR(KBr): 1756, 1652 cm$^{-1}$ Elementaranalyse: $C_{11}H_{11}N_4O_5SNa$ Calc. C 39.52 H 3.32 N 16.67 S 9.59 Found. C 39.66 H 3.17 N 16.81 S 9.55

EXAMPLE 9

R(α)-[[(1S,5R)-7-Oxo-6-sulpho-2,6-diazabicyclo[3.2.0]hept-2-yl]carbonyl]benzyl sulphate sodium salt was made in analogy to Example 1 a, but using a two-fold amount of DMF.SO₃ complex for the sulphonation.

IR (KBr): 1760, 1649 cm⁻¹

The (1S,5R)-2-[(R)-hydroxyphenylacetyl]-7-oxo-2,6-diazabicyclo[3.2.0]heptane used as the starting material was prepared from (1S,5R)-2,6-diazabicycio[3.2.0]heptane-7-one in analogy to Example 6a.

NMR (250 MHz, δ ppm, DMSO-d₆): 1.42–1.5 (m,1H) 1.80(m,1H), 3.15 (m,1H), 4.05 (m,1H), 4.3 and 5.55 (2t,J= 5.6 Hz,1H), 5.3 (d,J=4 Hz,1H) 5.3 and 5.4 (2d,J=6,5 Hz,1H), 5.82 and 5.97 (2d,J=6.5 Hz,1H), 7.2–7.5 (m,5H), 8.13 and 8.22 (2s broad, 1H).

EXAMPLE 10

(1S,5R)-2-(2-Amino-4-thiazolglyoxyloyl)-7-oxo-2,6-diazabicyclo[3.2.0]heptane-6-sulphonic acid sodium salt A solution of (1S,5R)-7-oxo-2,6-diazabicyclo[3.2.0] heptane-6-sulphonic acid (170 mg, 0.49 mmol) in water (20 ml) was treated with sodium bicarbonate (40 mg, 0.5 mmol). The solution was diluted with THF (20 ml) and treated with S-(2-benzothiazolyl)-2-aminothio-4-thiazolglyoxylate (346 mg, 0.53 mmol). After stirring for 24 hours the THF was evaporated and the aqueous phase was extracted with methylene chloride. The aqueous phase was chromatographed over a polymeric hydrophobic gel (eluent water, then water-:methanol 4:1). The fractions containing the product were combined and lyophilized.

Yield 240 mg (66%).

Elementary analysis: $C_{10}H_9N_4O_6S_2Na$ Calc. C 32.61 H 2.46 N 15.21 S 17.41 Found C 32.93 H 2.57 N 15.39 S 17.75

EXAMPLE 11

(a) (1S,5R)-(E)-3-Phenyl-acryloyl-2,6-diazabicyclo [3.2.0]heptane-6-sulphonic acid sodium salt was manufactured by sulphonylation in the same manner as described in Example 1

IR (KBr): 1756, 1650 cm⁻¹

Elementary analysis: $C_{14}H_{13}N_2O_5S_2Na$ Calc. C 48.84 H 3.81 N 8.14 Found C 48.84 H 3.85 N 8.16

The (1S,5R)-(E)-3-phenyl-acryloyl-2,6-diazabicyclo [3.2.0]-heptan-7-one used for this was prepared as follows:

(1S,5R)-2,6-Diazabicyclo[3.2.0]heptan-7-one (Example 2) (500 mg, 4.5 mmol) were suspended in 50 ml of dichloromethane. 0.75 ml (5.4 mmol) of triethylamine and subsequently 890 mg (5.4 mmol) of cinnamoyl chloride were added dropwise thereto while cooling with ice and the mixture was left to stir for 30 minutes while cooling and for 3.5 hours at room temperature. Thereafter, it was extracted once each time with saturated aqueous sodium carbonate solution, 2% aqueous citric acid solution, water and saturated aqueous sodium chloride solution. The combined organic phases were dried over magnesium sulphate and concentrated. Purification was effected by flash chromatography over silica gel with ethyl acetate. Yield: 560 mg (52%).

IR(KBr): 1752, 1648 cm⁻¹
MS (EI): 199 (M–CONH)⁺.

In the same manner there were made:

(b) (1S,5R)-7-Oxo-2-(3-phenyl-propionyl)-2,6-diazabicyclo-[3.2.0]heptane-6-sulphonic acid sodium salt IR(KBr): 1756, 1640 cm⁻¹

Elementary analysis $C_{14}H_{15}N_2O_5S_2Na$ Calc. C 46.55 H 4.37 N 8.09 Found C 48.30 H 4.66 N 7.75

(c) (1S,5R)-2-[(E)-3,4-Bis(sulphoxy)cinnamoyl]-7-oxo-2,6-diazabicyclo[3.2.0]heptane-6-sulphonic acid sodium salt (prepared using a three-fold amount of dimethylformamide-sulphur trioxide complex)

IR (KBr): 1758, 1648 cm⁻¹

¹H-NMR (250 MHz, DMSO-d₆): (rotamers in the ratio of about 3:2) δ [ppm]=1.72 (4-H, m, br, 1H); 2.34 (4-H, m, br, 1H); 3.16 (3-H, m, br, 1H); 4.16 (3-H, dd, br, 1H); 4.30 (3-H, dd, br, 1H); 4.36 (5-H, t, br, 1H); 4.50 (5-H, t, br, 1H); 5.36 (1-H, d, 1H, J=5 Hz); 5.51 (1-H, d, 1H, J=5 Hz); 6.84 (CH=, d, 1H,J=15 Hz); 7.36 (1H arom., br, s); 7.40 (CH=, 1H, J=15 Hz); 7.60 (1H arom., d, J=9 Hz); 7.71 (1H atom., s, br).

(d) (1S,5R)-2-(Benzylsulphonyl)-7-oxo-2,6-diazabicyclo [3.2.0]heptane-6-sulphonic acid sodium salt IR (KBr): 1764 cm⁻¹

Elementary analysis: $C_{12}H_{13}N_2O_6S_2Na$ Calc. C 39.13 H 3.56 N 7.61 S 17.41 Found C 39.24 H 3.52 N 7.64 S 17.13

EXAMPLE 12

(a) (1S,5R)-2-[(E)-p-Aminocinnamoyl]-7-oxo-2,6-diazabicyclo-[3.2.0]heptane-6-sulphonic acid 200 mg (0.46 mmol) (1S,5R)(E)-2-[3-(4-chloroacetylaminophenyl)acryloyl]-7-oxo-2,6-diazabicyclo [3.2.0]heptane-6-sulphonic acid sodium salt and 35 mg (0.46 mmol) of finely pulverized thiourea in 5 ml of ethanol were held at room temperature for 5 minutes, at 60° C. for 18 hours and under reflux for 1 hour. There was obtained a greenish-yellow suspension which was concentrated and treated with 4 ml of water. The pH was adjusted to 3–4 and the mixture was heated to 100° C. for 40 minutes. The yellow solution which thereby results was extracted three times with ethyl acetate, the aqueous phase was concentrated and purified over a hydrophobic gel column. Yield: 42 mg (27%).

IR (KBr): 1758, 1642 cm⁻¹
MS (ISN): 336.1 (M–H)⁻

The (1S,5R)(E)-2-[3-(4-chloroacetylaminophenyl) acryloyl]-7-oxo-2,6-diazabicyclo[3.2.0]heptane-6-sulphonic acid used as the starting material was prepared as follows:

(E)-3-(4-Chloroacetylaminophenyl)acrylic acid

4-Aminocinnamic acid hydrochloride (5 g, 25 mmol) were suspended in 30 ml of methylene chloride, cooled to 8° C. and treated with 3 ml of pyridine and 4.47 g (26 mmol) of chloroacetic anhydride. The mixture was then left to stir at room temperature overnight. The suspension was suction filtered and the filter cake was washed in water and filtered. Yield: 5.1 g (85%).

IR (KBr): 1686, 1659 cm⁻¹

Elementary analysis: $C_{11}H_{10}ClNO_3$ Calc. C 55.13 H 4.21 N 5.84 Found C 55.40 H 4.11 N 5.74

(1S,5R)-(E)-2-Chloro-N-[4-[3-oxo-3-(7-oxo-2,6-diazabicyclo-[3.2.0]hept-2-yl)propenyl]phenyl] acetamide (E)-3-(4-Chloroacetylaminophenyl)acrylic acid (1.44 g, 6.0 mmol) was suspended in 50 ml of tetrahydrofuran, treated with 0.66 ml (6.0 mmol) of N-methylmorpholine and cooled to −10° C. Subsequently, 0.8 ml (6.0 mmol) of isobutyl chloroformate was added dropwise thereto, the mixture was stirred for 30 minutes while cooling and then, at room temperature overnight. The solvent was removed in a vacuum, the residue was taken up in ethyl acetate and extracted twice with water and once with saturated aqueous sodium chloride solution. The organic phase was dried over magnesium sulphate and concentrated. The thus-obtained mixed anhydride was diluted in 25 ml of dichloromethane and added dropwise to a solution of 500 mg (4.5 mmol) of (1S,5R)-2,6-diazabicycio[3.2.0]heptan-7-one (Example 2) dissolved in 25 ml of dichloromethane and 4 ml of dimethylformamide. The mixture was left to react overnight and the product which separates was filtered off under suction. The latter was purified by chromatography (silica gel, 1. ethyl acetate, 2. ethyl acetate/ethanol=3:2). Yield: 1.0 g (50%).

IR (KBr): 1756, 1696, 1651 cm$^{-1}$
MS (ISP): 334.3 (M+H)$^+$ (1S,5R)(E)-2-[3-(4-Chloroacetylaminophenyl) acryloyl]-7-oxo-2,6-diazabicyclo[3.2.0]heptane-6-sulphonic acid sodium salt This compound was prepared from (1S,5R)-(E)-2-chloro-N-[4-[3-oxo-3-(7-oxo-2,6-diazabicyclo[3.2.0]hept-2-yl) propenyl]phenyl]acetamide analogously to the method described in Example 1 (sulphonation).

IR (KBr): 1757, 1686 cm$^{-1}$
MS (ISN): 412.0 (M−Na)$^-$

In the same manner there was made:

(b) (1S,5R)-7-Oxo-2-(1,2,4-triazol-3-yl-thioacetyl)-2,6-diazabicyclo[3.2.0]heptane-6-sulphonic acid IR (KBr): 1756, 1636 cm$^{-1}$
MS (ISN): 332.0 (M−H)$^-$

EXAMPLE 13

4-[(E)-2-[[(1S,5R)-7-Oxo-6-sulpho-2,6-diazabicyclo [3.2.0]heptan-2-yl]carbonyl]vinyl]-o-phenylene diacetate sodium salt was made by sulphonation in the same manner as given in Example 1

IR (KBr): 1764, 1650 cm$^{-1}$
MS: (M−Na)$^-$436.7

The 4-[(E)-2-[[(1S,5R)-7-oxo-2,6-diazabicyclo[3.2.0] heptan-2-yl]carbonyl]-vinyl]o-phenylene diacetate used for this Example was prepared as follows:

3-[3,4-Bis(acetoxy)phenyl]-2-propenoic acid anhydride (365 mg, 0.72 mmol) and (1S,5R)-2,6-diazabicyclo[3.2.0] heptan-7-one were stirred together in 5 ml of DMF at room temperature overnight. Thereafter, the solvent was removed at 70° C. in a high vacuum, the oily residue was taken up in water and extracted with ethyl acetate. The organic phase was dried over magnesium sulphate, concentrated and the crystalline residue which thereby separated was digested in ethyl acetate and filtered off under suction.

Yield: 120 mg (47%)
M.p.: 160°–165° C. (ethyl acetate)
IR (KBr): 1769, 1648 cm$^{-1}$

EXAMPLE 14

(a) (1S,5R)-(E)-4-Methoxycarbonylmethylene-7-oxo-6-sulpho-2,6-diazabicyclo[3.2.0]heptane-2-carboxylic acid benzyl ester sodium salt was made by sulphonation in the same manner as given in Example 1.

IR (KBr): 1749, 1700 cm$^{-1}$
MS (ISN): 395.1 (M−Na)$^-$

The (1S,5R)-(E)-4-methoxycarbonylmethylene-7-oxo-2,6-diazabicyclo[3.2.0]heptane-2-carboxylic acid benzyl ester used for this Example was prepared as follows:

Benzyl (1S,4S,5S)-4-hydroxy-7-oxo-2,6-diazabicyclo-[3.2.0]heptane-2-carboxylate was prepared from benzyl (1S,4S,5S)-4-hydroxy-6-(3,4-dimethoxybenzyl)-7-oxo-2,6-diazabicyclo-[3.2.0]heptane-2-carboxylate (Example 1) in the same manner as described for benzyl (1S,5R)-7-oxo-2,6-diazabicyclo[3.2.0]heptane-2-carboxylate (Example 1).

IR (KBr): 1764, 1720, 1660 cm$^{-1}$
Elementary analysis: C$_{13}$H$_{14}$N$_2$O$_4$ Calc. C 59.54 H 5.38 N 10.68 Found C 59.47 H 5.50 N 10.38

(1S,4S,5S)-2-Benzyloxycarbonyl-4-[(R)- and (S)-tetrahydropyran-2-yloxy]-2,6-diazabicyclo[3.2.0] heptan-7-one (1:1 mixture)

Benzyl (1S,4S,5S)-4-hydroxy-7-oxo-2,6-diazabicyclo-[3.2.0]heptane-2-carboxylate (40.0 g, 153 mmol) was placed in 500 ml of dimethylformamide, treated with 2.9 g (15 mmol) of p-tohenesulphonic acid monohydrate and treated with 28 ml (305 mmol) of dihydropyran. After a reaction period of 24 hours the solvent was removed in a high vacuum and the residual brown oil was purified by chromatography [silica gel, ethyl acetate/n-hexane (3:2)].

Yield: 40 g (76%)
IR (film): 1775, 1714 cm$^{-1}$
MS (CI): 364 (M+NH4)$^+$ (1S,4S,5S)-6-(t-Butyl-dimethyl-silanyl)-4-[(R)- and (S)-tetrahydropyran-2-yloxy]-7-oxo-2,6-diazabicyclo[3.2.0]heptane-2-carboxylic acid benzyl ester (1:1 mixture)

(1S,4S,5S)-2-Benzyloxycarbonyl-4-[(R)- and (S)-tetrahydropyran-2-yloxy]-2,6-diazabicyclo[3.2.0]heptan-7-one (1:1 mixture) (39.85 g 115 mmol) was dissolved in 800 ml of dichloro-methane, treated with 24.1 ml (173 mmol) of triethylamine and 26.0 g (173 mmol) of t-butyl-dimethylchlorosilane and stirred at room temperature for 24 hours. Thereafter, the reaction mixture was extracted twice with water and once with saturated aqueous sodium chloride solution, dried over magnesium sulphate and concentrated. Purification was effected by chromatography over silica gel with ethyl acetate/n-hexane (3:2).

Yield: 46.8 g (88%)
IR (film): 1757, 1711 cm$^{-1}$
MS (CI): 478 (M+NH4)$^+$

Benzyl (1S,4S,5S)-6-(t-butyl-dimethyl-silanyl)-4-hydroxy-7-oxo-2,6-diazabicyclo[3.2.0]heptane-2-carboxylate.

2.6 g (5.64 mmol) of (1S,4S,5S)-6-(t-butyl-dimethyl-silanyl)-4-[(R)- and (S)-tetrahydropyran-2-yloxy]-7-oxo-2,6-diazabicyclo[3.2.0]heptane-2-carboxylic acid benzyl ester (1:1 mixture) were treated with 140mg (0.56 mmol) of pyridinium p-toluenesulphonate in 75 ml of methanol at 50° C. for one day. Thereafter, the solvent was removed in a vacuum and the oily residue was purified by column chromatography (140 g of silica gel, particle size 0.04–0.063 mm, ethyl acetate/n-hexane=2:1). There was obtained a colourless oil which crystallized upon standing.

Yield: 1.39 g (65%)
M.p. 99.5°–101° C.
Elementary analysis: C$_{19}$H$_{28}$N$_2$O$_4$Si Calc. C 60.61 H 7.50 N 7.44 Found C 60.48 H 7.64 N 7.32

(1S,5S)-6-(t-Butyl-dimethyl-silanyl)-4,7-dioxo-2,6-diazabicyclo[3.2.0]heptane-2-carboxylic acid benzyl ester was prepared from benzyl (1S,4S,5S)-6-(t-butyldimethylsilanyl)-4-hydroxy-7-oxo-2,6-diazabicyclo[3.2.0]heptane-2-carboxylate in the same manner as described for benzyl (1S,5S)-6-(3,4-dimethoxybenzyl)-4,7-dioxo-2,6-diazabicyclo[3.2.0.]heptane-2-carboxylate (Example 7).

IR (film): 1760, 1712 cm$^{-1}$
MS(FAB): 505.2 (M+Na)$^+$ (1S,5R)(E)-6-(t-Butyl-dimethyl-silanyl)-4-methoxycarbonylmethylene-7-oxo-2,6-diazabicyclo[3.2.0]heptane-2-carboxylic acid benzyl ester 327 mg (7.37 mmol) of sodium hydride (55% suspension in mineral oil) were suspended in 30 ml of absolute toluene and cooled to 12° C. under argon. 1.34 g (7.37 mmol) of trimethyl phosphonoacetate were added dropwise thereto and the mixture was left to react for 1.5 hours. Thereafter, 2.76 g (7.37 mmol) of (1S,5S)-6-butyldimethyisilanyl)-4,7-dioxo-2,6-diazabicyclo[3.2.0]heptane-2-carboxylic acid benzyl ester dissolved in 30 ml of toluene were added dropwise in such a manner that the temperature did not exceed 30° C. Subsequently, the mixture was stirred at room temperature for 30 minutes and at 65° C. for 1 hour. Water was then added thereto and the mixture was extracted three times with saturated aqueous sodium hydrogen carbonate solution and once with saturated aqueous sodium chloride solution. After drying over magnesium sulphate and removing the solvent in a vacuum there was obtained an oil which was purified by chromatography (silica gel, ethyl acetate/n-hexane=2:1).

Yield: 2.17 g (68%)
IR (film): 1756, 1716 cm$^{-1}$
MS (CI): 448 (M+NH$_4^+$)

(1S,5R)(E)-4-Methoxycarbonylmethylene-7-oxo-2,6-diazabicyclo[3.2.0]heptane-2-carboxylic acid benzyl ester (1S,5R)(E)-6-(t-Butyl-dimethylsilanyl)-4-methoxycarbonylmethylene-7-oxo-2,6-diazabicyclo[3.2.0]heptane-2-carboxylic acid benzyl ester (2.13 g, 4.95 mmol) in 30 ml of methanol was stirred at room temperature for 75 minutes together with 183 mg (4.95 mmol) of ammonium fluoride. The solution was concentrated in a vacuum and the residue was taken up in ethyl acetate. The solution was extracted twice with water and once with saturated aqueous sodium chloride solution, the organic phase was dried over magnesium sulphate and the solvent was removed in a vacuum.

Yield: 1.32 g (84%)
IR (KBr): 1774, 1713 cm$^{-1}$
MS (ISP): 334.1 (M+NH$_4^+$)

In an analogous manner there were made:

b) (1S,5R)(E)-2-Benzyloxycarbonyl-4-carbamoylmethylene-7-oxo-2,6-diazabicyclo[3.2.0]heptane-6-sulphonic acid sodium salt (using triphenylphosphoranylideneacetamide in place of trimethyl phosphonoacetate)

IR (KBr): 1768, 1693, 1655 cm$^{-1}$
Elementary analysis: C$_{15}$H$_{14}$N$_3$O$_7$SNa Calc. C 44.67 H 3.50 N 10.42 S 7.95 Found C 44.91 H 3.49 N 10.47 S 7.66 c) (1S,5R)(Z)-2-Benzyloxycarbonyl-4-carbamoylmethylene-7-oxo-2,6-diazabicyclo[3.2.0]heptane-6-sulphonic acid sodium salt IR (KBr): 1769, 1694, 1659 cm$^{-1}$
MS 380.1 (M$^-$)

Elementary analysis: C$_{15}$H$_{14}$N$_3$O$_7$SNa Calc. C 44.67 H 3.50 N 10.42 S 7.95 Found C 45.24 H 3.63 N 10.46 S 7.73

EXAMPLE 15

(1S,4R,5S)-2-Benzyloxycarbonyl-4-chloro-7-oxo-2,6-diazabicyclo-[3.2.0]heptane-6-sulphonic acid sodium salt was made by sulphonating (1S,4R,5S)-4-chloro-7-oxo-2,6-diazabicyclo[3.2.0]heptane-2-carboxylic acid benzyl ester in the same manner as given in Example 1

IR (KBr): 1770, 1710 cm$^{-1}$
MS (ISN): 359.0 (M—Na)$^-$

The (1S,4R,5S)-4-chloro-7-oxo-2,6-diazabicyclo[3.2.0]heptane-2-carboxylic acid benzyl ester used for this Example was prepared as follows:

(1S,4R,5S)-6-(t-Butyl-dimethylsilanyl)-7-oxo-4-trifluoromethanesulphonyloxy-2,6-diazabicyclo[3.2.0]heptane-2-carboxylic acid benzyl ester Benzyl (1S,4S,5S)-6-(t-butyl-dimethylsilanyl)-4-hydroxy-7-oxo-2,6-diazabicyclo[3.2.0]heptane-2-carboxylate (Example 14) (5.0 g, 13.28 mmol) was dissolved in 50 ml of dichloromethane together with 1.18 ml (14.61 mmol) of pyridine and cooled to −3° C. A solution of 2.46 ml (14.61 mmol) of trifluoromethane-sulphonic anhydride in 5 ml of dichloromethane was slowly added dropwise thereto, whereby the temperature would not rise higher than 0° C. The reaction mixture was left to stir for 2 hours while cooling and was thereafter extracted in each case once with dilute aqueous sodium hydrogen carbonate solution, water and saturated aqueous sodium chloride solution. After filtration of the organic phase through a hydrophobic fluted filter and concentration in a vacuum there was obtained an orange coloured oil.

Yield: 6.0 g (89%)
IR (film): 1765, 1716 cm$^{-1}$
MS (ISP): 526.4 (M+NH$_4^+$)

(1S,4R,5S)-4-Chloro-7-oxo-2,6-diazabicyclo[3.2.0]heptane-2-carboxylic acid benzyl ester (1S,4R,5S)-6-(t-Butyl-dimethylsilanyl)-7-oxo-4-trifluoromethanesulphonyloxy-2,6-diazabicyclo[3.2.0]heptane-2-carboxylic acid benzyl ester (509 mg, 1 mmol) and tetrabutylammonium chloride (695 mg, 2.5 mmol) were stirred together in 5 ml of dimethylformamide at 60° C. for 2 hours. Thereafter, the solvent was removed in a vacuum and the residue was purified by chromatography (silica gel, ethyl acetate/n-hexane=2:1).

Yield: 76 mg (27%)
IR (film):1774, 1707 cm$^{-1}$
MS (CI): 298 (M+NH$_4^+$)

EXAMPLE 16

(a) (1S,4S,5S)-4-Fluoro-7-oxo-6-sulpho-2,6-diazabicyclo-[3.2.0]heptane-2-carboxylic acid benzyl ester sodium salt was made by sulphonation in the same manner as described in Example 1

IR (KBr): 1769, 1698 cm$^{-1}$
Elementary analysis: C$_{13}$H$_{12}$FN$_2$O$_6$SNa Calc. C 42.63 H 3.30 N 7.65 S 8.75 Found C 42.23 H 3.47 N 7.58 S 8.59

The (1S,4S,5S)-4-fluoro-7-oxo-2,6-diazabicyclo[3.2.0]heptane-2-carboxylic acid benzyl ester used for this Example was prepared as follows:

Benzyl (1S,4R,5S)-6-(3,4-dimethoxybenzyl)-4-hydroxy-7-oxo-2,6-diazabicyclo[3.2.0]heptane-2-carboxylate 1.8 g (4.4 mmol) of benzyl (1S,5S)-6-(3,4-dimethoxybenzyl)-4,7-dioxo-2,6-diazabicyclo[3.2.0]heptane-2-carboxylate (Example 7) were dissolved in 50 ml of ethanol and 166 mg (4.4 mmol) of sodium borohydride were added thereto while cooling with ice. Subsequently, the mixture was stirred at room temperature overnight, acidified with glacial acetic acid and the solvent was removed in a vacuum. The oily residue was taken up in methylene chloride, washed once each time with saturated aqueous sodium hydrogen carbonate solution and water, dried over magnesium sulphate and concentrated. By filtration with ethyl acetate over a short silica gel column (Merck, 0.063–0.2 mm) there was obtained a colourless oil which crystallized upon standing.

Yield: 1.2 g (66%)
M.p.: 118°–120° C.
Elementary analysis: $C_{22}H_{24}N_2O_6$ Calc. C 64.07 H 5.87 N 6.79 Found C 64.07 H 5.95 N 6.82

(1S,4R,5S)-6-(3,4-Dimethoxybenzyl)-7-oxo-4-trifluoromethanesulphonyloxy-2,6-diazabicyclo[3.2.0]heptane-2-carboxylic acid benzyl ester was prepared from benzyl (1S,4R,5S)-4-hydroxy-6-(3,4-dimethoxybenzyl)-7-oxo-2,6-diazabicyclo-[3.2.0]heptane-2-carboxylate analogously to (1S,4S,5S)-6-(t-butyldimethyl-silanyl)-7-oxo-4-trifluoromethanesulphonyloxy-2,6-diazabicyclo[3.2.0]heptane-2-carboxylic acid benzyl ester (Example 14).

IR (KBr): 1772, 1713 $cm^{-1}$
MS (EI): 544 ($M^+$)

(1S,4S,5S)-4-Fluoro-6-(3,4-dimethoxybenzyl)-7-oxo-2,6-diazabicyclo[3.2.0]heptane-2-carboxylic benzyl ester (1S,4R,5S)-6-(3,4-Dimethoxy-benzyl)-7-oxo-4-trifluoromethanesulphonyloxy-2,6-diazabicyclo[3.2.0]heptane-2-carboxylic acid benzyl ester (1.1 g, 2.02 mmol) and tetrabutylammonium fluoride trihydrate (704 mg, 2.23 mmol) were stirred together in 10 ml of tetrahydrofuran at room temperature for 10 min. Thereafter, the solvent was removed in a vacuum, the oily residue was taken up in ethyl acetate and extracted three times with water and once with saturated aqueous sodium chloride solution. The organic phase was dried over magnesium sulphate and concentrated. The residual brown oil was chromatographed over silica gel with ethyl acetate and a pale yellow oil was obtained.

IR (film): 1764, 1708 $cm^{-1}$
MS (ISP): 437.2 $(M+Na)^+$ (1S,4S,5S)-4-Fluoro-7-oxo-2,6-diazabicyclo[3.2.0]heptane-2-carboxylic acid benzyl ester was prepared from (1S,4S,5S)-4-fluoro-6-(3,4-dimethoxybenzyl)-7-oxo-2,6-diazabicyclo[3.2.0]heptane-2-caxboxylic acid benzyl ester analogously to benzyl (1S,5R)-7-oxo-2,6diazabicyclo[3.2.0]heptane-2-carboxylate (Example 1).

IR (film): 1772, 1707 $cm^{-1}$
MS (ISN): 263.1 $(M-H)^-$

In analogy thereto there was made:

(b) (1S,4R,5S)-2-Benzyloxycarbonyl-4-chloro-7-oxo-2,6-diazabicyclo[3.2.0]heptane-6-sulphonic acid sodium salt IR (KBr): 1769, 1710 $cm^{-1}$
MS (ISP): 359.0 ($M^-$)

EXAMPLE 17

(a) (1S,5R)-2-(2-Furan-2-yl-methylcarbamoyl)-7-oxo-2,6-diazabicyclo[3.2.0]heptane-6-sulphonic acid sodium salt A solution of (1S,5R)-7-oxo-2,6-diazabicyclo[3.2.0]-heptane-6-sulphonic acid (Example 6; 192 mg, 1 mmol) in water (5 ml) was treated with sodium bicarbonate (84 mg, 1 mmol). After 10 minutes a solution of 2,5-dioxo-tetrahydropyrrol-1-yl furan-2-yl-methylcarbamate (250 mg, 1.05 mmol) in acetonitrile was added and the mixture was stirred for a further 3 hours. The organic solvent was removed in a vacuum and the aqueous phase obtained was purified over a polymeric hydrophobic gel. The fractions containing the product were purified and lyophilized.

Yield: 193 mg (57%).
IR (KBr):1745, 1639 $cm^{-1}$
Elementary analysis: $C_{11}H_{13}N_3O_6SNa$ Calc. C 39.17 H 3.59 N 12.46 Found C 39.20 H 3.61 N 12.45

The 2,5-dioxo-tetrahydropyrrol-1-yl furan-2-yl-methylcarbamate used above was prepared as follows:

N,N'-Disuccinimidocarbonate (0.48 g, 5 mmol) was dissolved in acetonitrile and treated with furfurylamine (2.5 g, 10 mmol). The mixture was left to stir for a further 2 hours and thereafter the solvent was evaporated. The residue was dissolved in methylene chloride and washed with water. The organic phase was dried over magnesium sulphate and crystallized from methylene chloride/n-hexane.

M.p.: 115°–116° C.
IR (KBr): 1765, 1738 $cm^{-1}$
Elementary analysis: $C_{10}H_{10}N_2O_5$ Calc. C 50.42 H 4.23 N 11.76 Found C 50.10 H 4.17 N 11.60

In analogy to Example 17(a) there were made:

(b) (1S,5R)-7-Oxo-2-[2-(pyridin-2-yl)ethylcarbamoyl]-2,6-diazabicyclo[3.2.0]heptane-6-sulphonic acid sodium salt IR (KBr): 1756, 1638 $cm^{-1}$
MS: 339 (M–Na)

(c) (1S,5R)-7-Oxo-2-[(2-pyridylmethyl)carbamoyl]-2,6-diazabicyclo[3.2.0]heptane-6-sulphonic acid sodium salt IR (KBr): 1754, 1640 $cm^{-1}$
MS: 325 (M–Na)

(d) (1S,5R)-7-Oxo-2-(2-phenyl-carbazoyl)-2,6-diazabicyclo-[3.2.0]heptane-6-sulphonic acid sodium salt IR (KBr): 1755, 1650 $cm^{-1}$
MS=325 (M–Na)
Elementary analysis: $C_{12}H_{13}N_4O_5SNa$ Calc. C 41.38 H 3.76 N 16.09 Found C 41.60 H 3.77 N 16.16

(e) (1S,5R)-2-(3,4-Dihydroxybenzylcarbamoyl)-7-oxo-2,6-diazabicyclo[3.2.0]heptane-6-sulphonic acid sodium salt IR (KBr): 755, 1634 $cm^{-1}$
MS=356 (M–Na)
Elementary analysis: $C_{13}H_{14}N_3O_7SNa$ Calc. C 41.16 H 3.72 N 11.08 Found C 41.35 H 3.71 N 11.07

(f) (1S,5R)-2-(3-Hydroxy-5,6-dimethyl-pyridazin-4-yl-methylcarbamoyl)-7-oxo-2,6-diazabicyclo[3.2.0]heptane-6-sulphonic acid sodium salt IR (KBr): 1755, 1648 $cm^{-1}$
MS=370 (M–Na)

Elementary analysis: $C_{13}H_{16}N_5O_6SNa$ Calc. C 39.70 H 4.10 N 17.80 Found C 39.93 H 4.53 N 17.70

(g) (1S,5R)-7-Oxo-2-(4-sulphamoyl-benzylcarbamoyl)-2,6-diazabicyclo[3.2.0]heptane-6-sulphonic acid sodium salt IR (KBr): 1755, 1639 cm$^{-1}$ Elementary analysis: $C_{13}H_{15}N_4O_7S_2Na$ Calc. C 36.62 H 3.55 N 13.14 Found C 37.01 H 3.43 N 13.19

(h) (1S,5R)-2-Cyclobutylcarbamoyl)-7-oxo-2,6-diazabicycio-[3.2.0]heptane-6-sulphonic acid sodium salt IR (KBr): 1755, 1637 cm$^{-1}$ Elementary analysis: $C_{10}H_{14}N_3O_5S$ Na Calc. C 38.58 H 4.53 N 13.50 Found C 38.62 H 4.45 N 13.47

(i) (1S,5R)-2-Cyclopropylcarbamoyl)-7-oxo-2,6-diazabicyclo[3.2.0]heptane-6-sulphonic acid sodium salt IR (KBr): 1754, 1640 cm$^{-1}$ Elementary analysis: $C_9H_{12}N_3O_5S$ Na (+0.78 mol of ethanol) Calc. C 38.07 H 5.05 N 12.60 Found C 37.83 H 5.37 N 12.45

(j) (1S,5R)-7-Oxo-2-(R,S)-(2-oxo-3-tetrahydrothienyl-carbamoyl)-2,6-diazabicyclo[3.2.0]heptane-6-sulphonic acid sodium salt IR (KBr): 1754, 1695, 1645 cm$^{-1}$ MS=333.9 (M−Na)

Elementary analysis: $C_{10}H_{12}N_3O_6S_2Na$ Calc. C 33.61 H 3.39 N 11.76 Found C 33.85 H 3.31 N 12.06

(k) (1S,5R)-2-[2-(3,4-Dihydroxyphenyl)ethylcarbamoyl]-7-oxo-2,6-diazabicyclo[3.2.0]heptane-6-sulphonic acid sodium salt IR (KBr): 1754, 1630 cm$^{-1}$ Elementary analysis: $C_{14}H_{16}N_3O_7SNa$ Calc. C 42.75 H 4.10 N 10.26 Found C 43.00 H 4.16 N 10.69

(l) (1S,5R)-2-(4-Methoxyphenylcarbamoyl)-7-oxo-2,6-diazabicyclo[3.2.0]heptane-6-sulphonic acid sodium salt IR (KBr): 1751, 1647 cm$^{-1}$ Elementary analysis: $C_{13}H_{14}N_3O_6SNa$ Calc. C 42:98 H 3.88 N 11.57 Found C 43.12 H 4.02 N 11.57

(m) (1S,5R)-2-Cyclohexylmethylcarbamoyl-7-oxo-2,6-diazabicyclo[3.2.0]heptane-6-sulphonic acid sodium salt IR (KBr): 1754, 1638 cm$^{-1}$ Elementary analysis: $C_{13}H_{20}N_3O_5SNa$ Calc. C 44.19 H 5.71 N 11.89 Found C 44.31 H 6.02 N 11.85

(n) (1S,5R)-7-Oxo-2-(thien-2-yl-methoxycarbonyl)-2,6-diazabicyclo[3.2.0]heptane-6-sulphonic acid sodium salt IR (KBr): 1758, 1705 cm$^{-1}$ Elementary analysis: $C_{11}H_{11}N_2O_6S_2Na$ Calc. C 37.29 H 3.13 N 7.91 Found C 37.46 H 3.11 N 7.96

(o) (1S,5R)-2-(1-Morpholinylcarbamoyl)-7-oxo-2,6-diazabicyclo[3.2.0]heptane-6-sulphonic acid sodium salt IR (KBr): 1756, 1650 cm$^{-1}$ Elementary analysis: $C_{10}H_{15}N_4O_6SNa$ Calc. C 35.09 H 4.42 N 16.37 Found C 35.11 H 4.41 N 16.33

(p) (1S,5R)-2-(2-Thien-2-ylmethylcarbamoyl)-7-oxo-2,6-diazabicyclo[3.2.0]heptane-6-sulphonic acid sodium salt IR (KBr): 1753, 1640 cm$^{-1}$ Elementary analysis: $C_{11}H_{12}N_3O_5S_2Na$ Calc. C 37.39 H 3.42 N 11.89 Found C 37.54 H 3.47 N 11.96

(q) (1S,5R)-2-(Furan-2-ylcarbonyl-carbazoyl)-7-oxo-2,6-diazabicyclo[3.2.0]heptane-6-sulphonic acid sodium salt IR (KBr): 1736, 1589 cm$^{-1}$ MS=343.1 (M−Na)

Elementary analysis: $C_{11}H_{11}N_4)_7SNa$ +5% $H_2O$ Calc. C 34.27 H 3.44 N 14.53 Found C 34.34 H 3.50 N 14.53

(r) (1S,5R)-2-[(R)-Hydroxy-2-oxo-pyrrolidin-3-yl-carbamoyl]-7-oxo-2,6-diazabicyclo[3.2.0]heptane-6-sulphonic acid sodium salt IR (KBr): 1758, 1703, 1637 cm$^{-1}$ MS=332.8 (M−Na)

Elementary analysis: $C_{10}H_{13}N_4O_7S_2Na$ Calc. C 33.71 H 3.68 N 15.73 Found C 33.34 H 3.95 N 15.87

(s) (1S,5R)-2-(3-Hydroxyphenylcarbamoyl)-7-oxo-2,6-diazabicyclo[3.2.0]heptane-6-sulphonic acid sodium salt IR (KBr): 1752, 1652 cm$^{-1}$ Elementary analysis: $C_{12}H_{12}N_3O_6SNa$ Calc. C 41.26 H 3.46 N 12.03 Found C 40.85 H 3.67 N 12.32

(t) (1S,5R)-7-Oxo-2-(S)-(2-oxo-3-tetrahydrothienyl-carbamoyl)-2,6-diazabicyclo[3.2.0]heptane-6-sulphonic acid sodium salt IR (KBr): 1754, 1695, 1646 cm$^{-1}$ MS=333.9 (M−Na)

Elementary analysis: $C_{10}H_{12}N_3O_6S_2Na$ Calc. C 33.61 H 3.39 N 11.76 Found C 33.67 H 3.33 N 11.78

(u) (1S,5R)-7-Oxo-2-(R)-(2-oxo-3-tetrahydrothienyl-carbamoyl)-2,6-diazabicyclo[3.2.0]heptane-6-sulphonic acid sodium salt IR (KBr): 1754, 1694, 1644 cm$^{-1}$ MS=333.9 (M−Na)

Elementary analysis: $C_{10}H_{12}N_3O_6S_2Na$ Calc. C 33.61 H 3.39 N 11.76 Found C 34.08 H 3.53 N 12.01

(v) (1S,5R)-2-(4-Dimethylaminobenzylcarbamoyl)-7-oxo-2,6-diazabicyclo[3.2.0]heptane-6-sulphonic acid sodium salt IR (KBr): 1752, 1638 cm$^{-1}$ Elementary analysis: $C_{13}H_{15}N_4O_7S_2Na$ Calc. C 36.62 H 3.55 N 13.14 Found C 37.01 H 3.43 N 13.19

(w) (1S,5R)-2-(4-Hydroxyphenylcarbamoyl)-7-oxo-2,6-diazabicyclo[3.2.0]heptane-6-sulphonic acid sodium salt IR (KBr): 1755, 1647 cm$^{-1}$ Elementary analysis: $C_{13}H_{15}N_4O_7S_2Na$ Calc. C 41.26 H 3.46 N 12.03 Found C 41.55 H 3.55 N 12.19

(x) (1S,5R)-2-[(R) and (S)-1,1-Dioxo-tetrahydrothiophen-3-ylcarbamoyl]-7-oxo-2,6-diazabicyclo[3.2.0]heptane-6-sulfonic acid sodium salt IR(KBr): 1756, 1640 cm$^{-1}$
MS=352.0 (M–Na)
Elementary analysis: $C_{10}H_{14}N_3O_7S_2Na$ calcd. C32.00 H3.76 N11.20 found C32.19 H3.76 N11.28

(y) (1S,5R)-2-[(R) and (S)-Tetrahydrofuran-2-ylmethyicarbamoyl]-7-oxo-2,6-diaza-bicyclo[3.2.0]heptane-6-sulfonic acid sodium salt IR(KBr): 1746, 1641 cm$^{-1}$
MS=318.3 (M–Na)
Elementary analysis: $C_{11}H_{16}N_3O_6SNa$ calcd. C38.71 H4.73 N12.31 found C38.52 H4.88 N12.48

(z) (1S,5R)-2-[1-Methyl-1H-tetrazol-5-ylmethylcarbamoyl]-7-oxo-2,6-diazabicyclo[3.2.0]heptane-6-sulfonic acid sodium salt IR(KBr): 1757, 1645 cm$^{-1}$
MS=330.2 (M–Na)
Elementary analysis: $C_9H_{12}N_7O_5SNa$ calcd. C30.60 H3.42 S9.07 found C31.37 H3.35 S8.77

(aa) (1S,5R)-2-[3-Methoxy-isoxazol-5-ylmethylcarbamoyl]-7-oxo-2,6-diazabicycio[3.2.0]heptane-6-sulfonic acid sodium salt IR(KBr): 1755, 1645 cm$^{-1}$
MS=345.2 (M–Na)
Elementary analysis: $C_{11}H_{13}N_4O_7SNa$ calcd. C35.87 H3.56 N15.21 found C36.12 H3.59 N15.23

(ab) (1S,5R)-2-[4-Hydroxy-benzylcarbamoyl]-7-oxo-2,6-diazabicyclo[3.2.0]heptane-6-sulfonic acid sodium salt IR(KBr): 1754, 1637 cm$^{-1}$
MS=340.1 (M–Na)
Elementary analysis: $C_{13}H_{14}N_3O_6SNa$ calcd. C42.98 H3.88 N11.57 found C43.07 H4.03 N11.86

(ac) (1S,5R)-2-Cyclopentylcarbamoyl-7-oxo-2,6-diazabicyclo[3.2.0]heptane-6-sulfonic acid sodium salt IR(KBr): 1754, 1636 cm$^{-1}$
MS=301.9 (M–Na)
Elementary analysis: $C_{11}H_{16}N_3O_5SNa$ calcd. C40.61 H4,96 N12.92 found C40.66 H4.98 N12.99

(ad) (1S,5R)-7-Oxo-2-(2-oxo-oxazolidin-3-ylcarbamoyl]-2,6-diazabicyclo[3.2.0]heptane-6-sulfonic acid sodium salt IR(KBr): 1759, 1663 cm$^{-1}$
MS=319.0 (M–Na)

(ae) (1S,5R)-2-(2-Amino-thiazol-4-ylmethylcarbamoyl]-7-oxo-2,6-diazabicyclo[3.2.0]heptane-6-sulfonic acid sodium salt IR(KBr): 1755, 1633 cm$^{-1}$
MS=346.2 (M–Na)
Elementary analysis: $C_{10}H_{12}N_5O_6S_2Na$ calcd. C32.52 H3.27 N18.96 found C32.80 H3.11 N18.67

(af) (1S,5R)-2-(3-Cyclopropyl-1,2,4-oxadiazol-5-ylmethylcarbamoyl)-7-oxo-2,6-diazabicyclo[3.2.0]heptane-6-sulfonic acid sodium salt IR(KBr): 1756, 1647 cm$^{-1}$
MS=356.2 (M–Na)
Elementary analysis: $C_{12}H_{14}N_5O_6SNa$ calcd. C38.00 H3.72 N18.16 found C38.06 H3.92 N18.56

(ag) (1S,5R)-7-Oxo-2-[(S)-2,5-dioxo-pyrrolidin-3-ylcarbamoyl]-2,6-diazabicyclo[3.2.0]heptane-6-sulfonic acid sodium salt IR(KBr): 1757, 1722, 1641 cm$^{-1}$
MS=331.1 (M–Na)
Elementary analysis: $C_{10}H_{11}N_4O_7SNa$ calcd. C33.90 H3.13 N15.82 found C34.03 H3.36 N16.00

EXAMPLE 18

Methyl (1S,5R)-7-oxo-6-sulpho-2,6-diazabicyclo[3.2.0]-heptane-2-carbamate sodium salt was made in analogy to Example 1 by sulphonating methyl-(1S,5R)-7-oxo-2,6-diazabicyclo[3.2.0]heptane-2-carbamate IR (KBr): 1749, 1268 cm$^{-1}$
MS: 286 (M–H), 264 (M–Na)

The methyl (1S,5R)-7-oxo-2,6-diazabicyclo[3.2.0]heptane-2-carbamate used above was prepared as follows:

A solution of (1S,5R)-2,6-diazabicyclo[3.2.0]heptan-7-one (Example 2, 0.4 g, 3.56 mmol) in acetonitrile was treated with N-methoxycarbonyl-3-phenyloxaziridine (0.7 g, 3.9 mmol) [J. Chem. Soc. Chem. Commun. 1991 435–437 (1983)] and stirred for two days. The solution was concentrated and the residue was washed three times with n-hexane; the n-hexane was decanted off each time. The residue was recrystallized from ethyl acetate/THF. Yield: 280 mg (43%).
M.p.:152°–55° C.
IR (KBr): 1751, 1704 cm$^{-1}$
Elementary analysis: $C_7H_{11}N_3O_3$ Calc. with 0.08 Mol THF C 46.04 H 6.14 N 22.01 Found C 45.72 H 6.10 N 21.81

EXAMPLE 19

(1S,5R)-7-Oxo-2-[2-(furan-2-ylmethoxycarbamoyl)propionyl]-2,6-diazabicyclo[3.2.0]heptane-6-sulphonic acid sodium salt was made in analogy to Example 17(a) starting from (1S,5R)-7-oxo-2,6-diazabicyclo[3.2.0]heptane-6-sulphonic acid and 1-(furan-2-ylmethoxy)-pyrrolidine-2,5-dione in DMF in the presence of sodium 2-ethylhexanoate. Yield 54%

IR (KBr): 1758, 1643 cm$^{-1}$
Elementary analysis: $C_{14}H_{17}N_3O_8SNa$ Calc. C 41.08 H 3.94 N 10.27 Found C 41.22 H 4.08 N 10.29

The 1-(furan-2-ylmethoxy)-pyrrolidine-2,5-dione used above was prepared in analogy to Example 17(a) starting from N,N'-disuccinimidocarbonate and 2-hydroxymethylfuran. Yield 47%.
Elementary analysis: $C_9H_9NO_4$ Calc. C 55.39 H 4.65 N 7.18 Found C 55.29 H 4.82 N 7.10

EXAMPLE 20

(1S,5R)-2-[[(3,4-Dihydroxyphenyl)sulphonyl]acetyl]-7-oxo-2,6-diazabicyclo[3.2.0]heptane-6-sulphonic acid sodium salt 1 g (1.69 mmol) of (1S,5R)-2-[[(2,2-diphenyl-1,3-benzodioxol-5-yl)sulphonyl]acetyl]-7-oxo-2,6-diazabicyclo

[3.2.0]heptane-6-sulphonic acid sodium salt in 100 ml of methanol/water=1:1 was treated with hydrogen for 1 hour in the presence of 550 mg of Pd/C 10% for 1 hour. The mixture was filtered, the filtrate was concentrated and separated over a hydrophobic gel column.

Yield: 100 mg (14%)

IR (KBr): 1760, 1642 cm$^{-1}$

Elementary analysis: $C_{13}H_{13}N_2O_9S_2Na$ Calc. C 36.45 H 3.06 N 6.54 S 14.97 Found C 36.59 H 3.08 N 6.57 S 14.75

The (1S,5R)-2-[[(2,2-diphenyl-1,3-benzodioxol-5-yl) sulphonyl]acetyl]-7-oxo-2,6-diazabicyclo[3.2.0]heptane-6-sulphonic acid used as the starting material was prepared by sulphonation in analogy to Example 1 or 5:

IR (KBr): 1744, 1653 cm$^{-1}$
MS (ISN): 569.0 (M−Na)

EXAMPLE 21

(1S,5R)-2-[(R,S)-Amino-(3,4-dihydroxyphenyl) acetyl]-7-oxo-2,6-diazabicyclo[3.2.0]heptane-6-sulphonic acid sodium salt was made starting from (1S,5R)-2-[(R,S)-t-butoxycarbonyl]amino-(3,4-dihydroxyphenyl)acetyl]-7-oxo-2,6-diazabicyclo [3.2.0]heptane-6-sulphonic acid sodium salt as in Example 6(b)

IR (KBr): 1765, 1659 cm$^{-1}$

Elementary analysis: $C_{13}H_{14}N_3O_7SNa$ Calc. C 43,70 H 4.23 N 11.76 Found C 43.79 H 4.12 N 11.48

The (1S,5R)-2-[(R,S)-t-butoxycarbonyl]amino-(3,4-dihydroxyphenyl)acetyl]-7-oxo-2,6-diazabicyclo[3.2.0] heptane-6-sulphonic acid sodium salt used for this Example was prepared as in Example 20 (hydrogenation) starting from (1S,5R)-2-[(R,S)-t-butoxycarbonyl]amino-2[(2,2-diphenyl-benzo[1,3]dioxol-5-yl)]acetyl]-7-oxo-2,6-diazabicycio[3.2.0]heptane-6-sulphonic acid sodium salt IR (KBr): 1760, 1702, 1652 cm$^{-1}$
MS=456 (M−Na)

The (1S,5R)-2-[(R,S)-t-butoxycarbonyl]amino-1[(2,2-diphenylbenzo[1,3]dioxol-5-yl)]acetyl-7-oxo-2,6-diazabicyclo[3.2.0]heptane-6-sulphonic acid sodium salt was prepared as in Example 1(a) (sulphonation) starting from t-butyl N-[(1R,S)-1-(2,2-diphenylbenzo[1,3]dioxol-5-yl)-2-oxo-2-((1S,5R)-7-oxo-2,6-diazabicyclo[3.2.0]hept-2-yl)ethyl]carbamate, yield 80%.

The t-butyl N-[(1R,S)-1-(2,2-diphenyl-benzo[1,3]dioxol-5-yl)-2-oxo-2-((1S,5R)-7-oxo-2,6-diazabicyclo[3.2.0]hept-2-yl)-ethyl]carbamate was synthesized analogously to Example 5(a):

M.p.: 198°–201° C.

Elementary analysis: $C_{31}H_{31}N_3O_6$ Calc. C 68.75 H 5.77 N 7.76 Found C 68.71 H 5.89 N 7.63

EXAMPLE 22

(1S,4R,5S)-2-Benzyloxycarbonyl-4-(1-methyl-1H-tetrazol-5-yl-thio)-7-oxo-2,6-diazabicyclo[3.2.0] heptane-6-sulphonic acid sodium salt was manufactured by sulphonation in the same manner as given in Example 1

IR (KBr): 1771, 1710 cm$^{-1}$
MS (ISN): 439.9 (M−Na)$^-$

The (1S,5S)-4-(1-methyl-1H-tetrazol-5-thio)-7-oxo-2,6-diazabicyclo[3.2.0]heptane-2-carboxylic acid benzyl ester used for this Example was prepared as follows:

(1S,4R,5S)-6-(t-Butyl-dimethylsilanyl)-7-oxo-4-trifluoromethanesulphonyloxy-2,6-diazabicyclo[3.2.0] heptane-2-carboxylic acid benzyl ester (1.9 g, 1.96 mmol) was dissolved in 20 ml DMF, treated with 600 mg (2.16 mmol) of 5-mercapto-1-methyltetrazole sodium salt hydrate and stirred at 80° C. under argon for 2 days. The solvent was removed, the residue was taken up in ethyl acetate and washed twice with water. The solution was dried over magnesium sulphate and chromatographed (silica gel, ethyl acetate). Yield: 150mg (21%).

IR (film): 1769, 1708 cm$^{-1}$
MS (ISP): 383.2 (M+Na)$^+$

EXAMPLE 23

(a) (1S,5R)'-2-(4-Methyl-2-oxo-2H-benzopyran-7-yloxyacetyl)-7-oxo-2,6-diazabicyclo[3.2.0]heptane-6-sulfonic acid sodium salt is manufactured by sulfonation in the same manner as described in Example 1

IR(KBr): 1759, 1715, 1661, 1615 cm$^{-1}$

Elementary analysis: $C_{17}H_{15}N_2O_8SNa$ calcd. C47.45 H3.51 N6.51 S7.45 found C47.44 H3.45 N6.54 S7.45

The (1S,5R)-2-(4-Methyl-2-oxo-2H-benzopyran-7-yloxy-acetyl)-2,6-diazabicyclo[3.2.0]heptane-2-one using as starting material can be manufactured as follows:

7-(Carboxymethoxy)-4-methyl-coumarin (1.0 g, 4.27 mmol) is stirred in 50 ml of DMF at room temperature with 0.6 ml (4.27 mmol) of triethylamine and 1.62 (4.27 mmol) of 0-benzotriazol-1-yl-N,N,N',N'-tetrmmethyl-uronium-hexafluorophosphate for 3 minutes. 400 mg (3.56 mmol) of diazabicyclo[3.2.0]heptane-7-one are added and reacted for 5 hours. The solvent is removed in high vacuum, and the oily residue is purified by chromatography over silica gel with ethanol:ethyl acetate 6:1.

Yield: 1.0 g (86%)
IR(KBr): 1758, 1724, 1690, 1614 cm$^{-1}$
MS(EI): 328 (M$^+$)

In the same manner, there are prepared:

(b) (1S,5R)-2-(4-Methyl-4H-1,2,4-triazol-3-ylsulfanylacetyl)-7-oxo-2,6-diazabicyclo[3.2.0] heptane-6-sulfonic acid sodium salt IR(KBr): 1758, 1644 cm$^{-1}$ Elementary analysis: $C_{10}H_{12}N_5O_5S_2Na$ calcd. C32.52 H3.27 N18.96 S17.36 found C32.78 H3.44 N18.99 S17.03

(c) (1S,5R)-2-[(E)-3-(1-Methyl -pyrrol-2-yl) acryloyl]-7-oxo-2,6-diazabicyclo[3.2.01]heptane-6-sulfonic acid sodium salt IR(KBr): 1756, 1640 cm$^{-1}$
MS (ISN): 324.2 (M$^-$)

(d) (1S,5R)-2-(1-Methyl-imidazol-2-ylsulfanylacetyl)-7-oxo-2,6-diazabicyclo[3.2.0] heptane-6-sulfonic acid sodium salt IR(KBr): 1757, 1642 cm$^{-1}$ Elementary analysis: $C_{11}H_{13}N_4O_5S_2Na$ calcd. C35.87 H3.56 N15.21 found C36.20 H3.69 N15.47

(e) (1S,5R)-7-Oxo-2-[(E)-3-pyrazol-3-yl-acryloyl]-2,6-diazabicyclo[3.2.0]heptane-6-sulfonic acid sodium salt IR(KBr): 1759, 1653, 1608 cm$^{-1}$
MS(ISN): 311.2 (M−Na)$^-$ (f) (1S,5R)-7-Oxo-(2-oxo -1,2-di hydro-pyrimidin-4-ylaminoaccytl)-2,6-diazabicyclo[3.2.0]heptane-6-sulfonic acid sodium salt IR(KBr): 1760, 1645 cm$^{-1}$
MS(ISN): 342.3 (M–Na)$^{-}$ (g) (1S,5R)-2-(5-Amino-2-benzyloxycarbonyl-2H-1,2,4-triazol-3-ylsulfanyl-acetyl)-7-oxo-2,6-diazabicyclo[3.2.0]heptane-6-sulfonic acid sodium salt IR(KBr): 1750, 1634 cm$^{-1}$
MS(ISN): 481.3 (M–Na)$^{-}$ (h) (1S,5R)-2-[(1R,3R)-2,2-Dimethyl-3-(2-methyl-propenyl)cyclopropylcarbonyl]7-oxo-2,6-diazabicyclo[3.2.0]heptane-6-sulfonic acid sodium salt IR(KBr): 1759, 1639 cm$^{-1}$
Elementary analysis: $C_{15}H_{21}N_2O_5SNa$ calcd. C49.44 H5.81 N7.69 S8.80 found C49.16 H5.88 N7.68 S8.62

(i) (1S,5R)-2-(5-Benzyloxycarbonylamino-1,3,4-thiadiazol-2-ylsulfanyl-acetyl)-7-oxo-2,6-diazabicyclo[3.2.0]heptane-6-sulfonic acid sodium salt IR(KBr): 1759, 1640 cm$^{-1}$
MS(ISN): 498.2 (M–Na)$^{-}$ (j) Mixture of (1S,5R)-2-[(E)-3-(1-Methyl-3- and -4- or -3- and -5- or-4- and -5-sulfo-pyrrol-2-yl) acryloyl]-7-oxo-2,6-diazabicyclo[3.2.0]heptane-6-sulfonic acid sodium salt (1:2)

IR(KBr): 1758, 1634 cm$^{-1}$
MS(ISN): 426.2 (M–Na)$^{-}$
Elementary analysis: $C_{13}H_{13}N_3O_8S_2Na_2$ calcd. C34.75 H2.29 N9.35 found C34.53 H2.67 N9.23

(k) Mixture of (1S,5R)-2-(5-Amino-1H-tetrazol-1-ylacetyl) and (1S,5R)-2-(5-Amino-2H-tetrazol-2-ylacetyl)-7-oxo-2,6-diazabicyclo[3.2.0]heptane-6-sulfonic acid sodium salt (1:2)

IR(KBr): 1760, 1660 cm$^{-1}$ (l) (1S,5R)-7-Oxo-2-[3-(1-sulfo-imidazol-5-yl) acryloyl]-2,6-diazabicyclo[3.2.0]heptane-6-sulfonic acid sodium salt IR(KBr): 1756, 1652, 1604 cm$^{-1}$
MS(ISN): 413.2 (M–Na)$^{-}$

EXAMPLE 24

Dry ampoules for intramuscular administration can be prepared as follows:

A lyophilizate of 0.5 g of the sodium salt of (1S,5R)-2-[D-2-(p-hydroxyphenyl)glycyl]-7-oxo-2,6-diazabicyclo[3.2.0]-heptane-6-sulphonic acid and 1 g of the disodium salt of (6R,7R)-7-[2-(2-amino-4-thiazolyl)-2-(Z-methoxyimino)-acetamido]-3-[(2,5-dihydro-6-hydroxy-2-methyl-5-oxo-as-triazin-3-yl)thio]methyl-8-oxo-5-thia-1-azabicyclo[4.3.0]oct-2-ene-2-carboxylic acid is prepared in the usual manner and filled into an ampoule. Prior to administration the lyophilizate is treated with 4 ml of a 2% aqueous lidocaine hydrochloride solution.

If desired, the two active ingredients can be filled separately into two different ampulles.

We claim:

1. A pharmaceutical composition for controlling illnesses caused by β-lactamase-forming pathogens comprising:

(a) a therapeutically effective amount of a compound having the formula

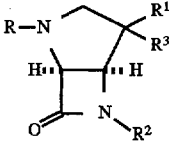

in which R signifies lower alkoxycarbonyl, lower alkoxycarbonylamino, the carboxylic acyl residue of an α- or β-amino acid, the amino group of said α- or β-amino acid being optionally substituted by lower alkyl, phenyl, lower alkanoyl, benzoyl, benzyloxycarbonyl, t-butoxycarbonyl, (4-ethyl-2,3-dioxo-1-piperazinyl) carbonyl or (4-hydroxy-6-methyl-3-pyridyl)carbonyl, or a residue of the formula Q—X—Y— (a)

wherein Q signifies a 3- to 6-membered ring which optionally contains 1–4 nitrogen atoms, and/or 1–2 sulphur or oxygen atoms and which is optionally substituted by hydroxy, halogen, lower alkyl, lower alkoxy, amino, lower alkanoyloxy, sulphonyloxy, dimethylamino or chloroacetylamino and which is optionally fused to a phenyl ring or a 5- or 6-membered heterocycle ring containing 1–3 nitrogen atoms or 1 oxgyen atom, X signifies a direct bond or represents one of —O—, —S—, —NH—, —NH—NH—, —CH$_2$—, —CO—, —CH$_2$O—, —CH$_2$CH$_2$—, —CH=CH—, —CH$_2$NH—, —S—CH$_2$—, —SO$_2$CH$_2$—, —O—CH$_2$—, —S—CH$_2$CH$_2$—, —CH$_2$CH$_2$—NH—, —CH$_2$—O—NH—CO—CH$_2$CH$_2$—, —CHOH—, —CH(COOH)—, —CH(OSO$_3$H)—, —CH(OCONH$_2$)—, and —CH[CH(CH$_3$)$_2$]—, and Y represents one of the groups —CO—, —CS—, —CONH— and —SO$_2$—, except that when Y is —SO$_2$—, X represents one of —O—, —NH—, —NH—NH—, —CH$_2$—, —CH$_2$O—, —CH$_2$CH$_2$—, —CH=CH—, —CH$_2$NH—, —O—CH$_2$—, —CH$_2$CH$_2$NH—, —CHOH—, and —CH[CH(CH$_3$)$_2$]—; and in which R$^1$ signifies hydrogen, halogen, carbamoyloxy, lower alkanoyloxy or a group of the formula —S—Het, wherein Het represents a 5- or 6-membered heteroaromatic group which contains 1–4 nitrogen atoms and/or 1 sulfur or oxygen atom and which is optionally substituted by lower alkyl, hydroxy, lower alkoxy, lower alkanoyloxy, halogen, amino, dimethylamino, or chloroacetylamino, R2 represents the sulpho group —SO$_3$H, and in which R$^3$ represents hydrogen or R$^1$ and R$^3$ together represent a group of the formula =CH—R$^a$ (c)

wherein R$^a$ signifies one of the groups

—COR$^b$ (c$^1$)

—CH$_2$—OCOR$^c$ (c$^2$)

—CH$_2$—NR$^d$R$^e$ (c$^3$)

—CH$_2$—S—Het (c$^4$)

in which $R^b$ represents lower alkoxy or amino, $R^c$ represents lower alkyl, phenyl or amino, $R^d$ and $R^e$ each independently represent hydrogen or lower alkyl or $R^d$ and $R^e$ together with the N atom to which they are attached represent a 5- or 6-membered N-heterocycle ring which optionally contains an additional nitrogen, oxygen or sulphur atom, said N-heterocycle ring optionally N-substituted or C-substituted by lower alkyl, and Het is as defined above,
or their pharmaceutically compatible salts; and (b) a therapeutically effective amount of a β-lactam antibiotic or their pharmaceutically compatible salts;

and a pharmaceutically acceptable carrier.

2. The pharmaceutical composition in accordance with claim 1 wherein the β-lactam antibiotic is selected from the group consisting of a penicillin or a cephalosporin or their respective pharmaceutically compatible salts.

3. The pharmaceutical composition in accordance with claim 2 wherein said penicillin is selected from the group consisting of benzylpenicillin, piperacillin, phenoxymethylpenicillin, carbenicillin, methicillin, propicillin, tricarcillin, ampicillin, amoxicillin, or mecillinam, or their pharmaceutically compatible salts.

4. The pharmaceutical composition in accordance with claim 2 wherein said cephalosporin is selected from the group consisting of ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylic acid- or (E)-2-(isobutyloxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylate or their pharmaceutically compatible salts.

5. The pharmaceutical composition in accordance with claim 4 wherein said cephalosporin is ceftriaxone or one of its pharmaceutically compatible salts.

6. The pharmaceutical composition of claim 2 wherein the ratio of the compound of formula I to β-lactam antibiotic is from about 1:20 to about 1:1.

7. The pharmaceutical composition in accordance with claim 5 wherein the compound of (a) is (1S,5R)-2-[D-2-(p-Hydroxyphenyl)glycyl]-7-oxo-2,6-diazabicyclo[3.2.0]heptane-6-sulphonic acid or its pharmaceutically compatible salts.

8. A method of inhibiting β-lactamase in mammals in need of such therapy which comprises administering (a) a therapeutically effective amount of a compound having the formula

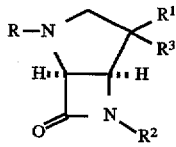

I in which R signifies lower alkoxycarbonyl, lower alkoxycarbonylamino, the carboxylic acyl residue of an α- or β-amino acid, the amino group of said α- or β-amino acid being optionally substituted by lower alkyl, phenyl, lower alkanoyl, benzoyl, benzyloxycarbonyl, t-butoxycarbonyl, (4-ethyl-2,3-dioxo-1-piperazinyl)carbonyl or (4-hydroxy-6-methyl-3-pyridyl)carbonyl, or a residue of the formula Q—X—Y— (a)

wherein Q signifies a 3- to 6-membered ring which optionally contains 1–4 nitrogen atoms, and/or 1–2 sulphur or oxygen atoms and which is optionally substituted by hydroxy, halogen, lower alkyl, lower alkoxy, amino, lower alkanoyloxy, sulphonyloxy, dimethylamino, or chloroacetylamino, and which is optionally fused to a phenyl ring or a 5- or 6-membered heterocycle ring containing 1–3 nitrogen atoms or 1 oxygen atom, X signifies a direct bond or represents one of —O—, —S—, —NH—, —NH—NH—, —CH$_2$—, —CO—, —CH$_2$O—, —CH$_2$CH$_2$—, —CH=CH—, —CH$_2$NH—, —S—CH$_2$—, —SO$_2$CH$_2$—, —O—, —CH$_2$—, —S—CH$_2$CH$_2$—, —CH$_2$CH$_2$—NH—, —CH$_2$—O—NH—CO—CH$_2$CH$_2$—, —CHOH—, —CH(COOH)—, —CH(OSO$_3$H)—, —CH(OCONH$_2$)—, and —CH[CH(CH$_3$)$_2$]—, and Y represents one of the groups —CO—, —CS—, —CONH— and —SO$_2$—, except that when Y is —SO$_2$—, X represents one of —O—, —NH—, —NH—NH—, —CH$_2$—, —CH$_2$O—, —CH$_2$CH$_2$—, —CH=CH—, —CH$_2$NH—, —O—CH$_2$—, —CH$_2$CH$_2$—NH—, —CHOH—, and —CH[CH(CH$_3$)$_2$]—;

and in which $R^1$ signifies hydrogen, halogen, carbamoyloxy, lower alkanoyloxy or a group of the formula —S—Het, wherein Het represents a 5- or 6-membered heteroaromatic group which contains 1–4 nitrogen atoms and/or 1 sulfur or oxygen atom and which is optionally substituted by lower alkyl, hydroxy, lower alkoxy, lower alkanoyloxy, halogen, amino, dimethylamino, or chloroacetylamino, and $R^2$ represents the sulpho group —SO$_3$H and in which $R^3$ represents hydrogen or $R^1$ and $R^3$ together represent a group of the formula $$=CH—R^a \quad (c)$$

wherein $R^a$ signifies one of the groups

—COR$^b$ (c$^1$)

—CH$_2$—OCOR$^c$ (c$^2$)

—CH$_2$—NR$^d$R$^e$ (c$^3$)

—CH$_2$—S—Het (c$^4$)

in which $R^b$ represents lower alkoxy or amino, $R^c$ represents lower alkyl, phenyl or amino, $R^d$ and $R^e$ each independently represent hydrogen or lower alkyl or $R^d$ and $R^e$ together with the N atom to which they are attached represent a 5- or 6-membered N-heterocycle ring which optionally contains an additional nitrogen, oxygen or sulphur atom, said N-heterocycle ring optionally N-substituted or C-substituted by lower alkyl, and Het is as defined above, or the pharmaceutically compatible salts thereof; and (b) a therapeutically effective amount of a β-lactam antibiotic or their pharmaceutically compatible salts;

and a pharmaceutically acceptable carrier.

9. The method of claim 8 wherein the β-lactam antibiotic is selected from the group consisting of penicillin or a cephalosporin or their respective pharmaceutically compatible salts.

10. The method of claim 8 wherein the ratio of the compound of formula I to β-lactam antibiotic is from about 1:20 to about 1:1.

11. The method of claim 9 wherein said penicillin is selected from the group consisting of benzylpenicillin, piperacillin, phenoxymethylpenicillin, carbenicillin, methicillin, propicillin, tricarcillin, ampicillin, amoxicillin, or mecillinam, or their pharmaceutically compatible salts.

12. The method of claim 11 wherein said cephalosporin is selected from the group consisting of ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R,7R)-7-[(Z)-2-(2-amino-4-thiazolyl)-2-(methoxyimino)acetamido]-3-(azidometyl)-8-oxo-5-thia-1-azabicyclo[4.2.01]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylate or their pharmaceutically compatible salts.

13. The method of claim 12 wherein said cephalosporin is ceftriaxone or one of its pharmaceutically compatible salts.

14. The method of claim 13 wherein the compound of (a) is (1S,5R)-2-[D-2-(p-Hydroxyphenyl)glycyl]-7-oxo-2,6-diazabicyclo[3.2.0]heptane-6-sulphonic acid or its pharmaceutically compatible salts.

* * * * *

UNITED STATES PATENT AND TRADEMARK OFFICE
CERTIFICATE OF CORRECTION

PATENT NO. : 5,698,577
DATED : December 16, 1997
INVENTOR(S) : Christian Hubschwerlen, Robert Charnas, Ingrid Heinze, Klaus Gubernator It is certified that error appears in the above-indentified patent and that said Letters Patent is hereby corrected as shown below:

In claim 1, column 56, line 52, delete "R2" and insert therefor -- $R^2$ --.

In claim 4, column 57, line 31, delete "[4.2.01]" and insert therefor -- [4.2.0] --.

In claim 4, column 57, line 32, delete "(isobutyloxycarbonyl)" and insert therefor -- (isobutoxycarbonyl) --.

In claim 9, column 58, line 55, between "of" and "penicillin" insert -- a --.

In claim 12, column 59, line 6, delete "(azidometyl)" and insert therefor -- (azidomethyl) --.

In claim 12, column 59, line 7, delete "[4.2.01]" and insert therefor -- [4.2.0] --.

Signed and Sealed this

Fourteenth Day of April, 1998

*Attest:*

BRUCE LEHMAN

*Attesting Officer*  *Commissioner of Patents and Trademarks*